US012573310B2

(12) United States Patent　　(10) Patent No.:　US 12,573,310 B2
Kravitz　　(45) Date of Patent:　Mar. 10, 2026

(54) SYSTEMS AND METHODS FOR USING A VOCATIONAL MASK WITH A HYPER-ENABLED WORKER

(71) Applicant: BlueForge Alliance, Bryan, TX (US)

(72) Inventor: Arnold Kravitz, St. Petersburg, FL (US)

(73) Assignee: BlueForge Alliance, Bryan, TX (US)

( * ) Notice: Subject to any disclaimer, the term of this patent is extended or adjusted under 35 U.S.C. 154(b) by 0 days.

(21) Appl. No.: 18/394,298

(22) Filed: Dec. 22, 2023

(65) Prior Publication Data

US 2025/0191483 A1　　Jun. 12, 2025

Related U.S. Application Data

(60) Provisional application No. 63/607,354, filed on Dec. 7, 2023.

(51) Int. Cl.
　　*G09B 5/06*　　(2006.01)
　　*A61F 9/06*　　(2006.01)
　　　　(Continued)
(52) U.S. Cl.
　　CPC ............... *G09B 5/065* (2013.01); *A61F 9/06* (2013.01); *G06F 3/016* (2013.01); *G06F 3/017* (2013.01);
　　　　(Continued)
(58) Field of Classification Search
　　CPC .................................................... G09B 5/065
　　See application file for complete search history.

(56) References Cited

U.S. PATENT DOCUMENTS 5,306,893 A　　4/1994　Morris et al.
7,962,967 B2　　6/2011　Becker et al.
　　　　(Continued)

FOREIGN PATENT DOCUMENTS

AU　　2022203028 A1　　5/2022
CN　　111653136 A　　9/2020
　　　　(Continued)

OTHER PUBLICATIONS

International Search Report and Written Opinion dtd Aug. 7, 2025 for PCT/US2025/026395, dtd Aug. 7, 2025, 10 pages.
　　　　(Continued)

*Primary Examiner* — Kesha Frisby
(74) *Attorney, Agent, or Firm* — Dickinson Wright PLLC; Jonathan H. Harder; Stephen A. Mason

(57) ABSTRACT

In one embodiment, a system includes a vocational mask configured to be worn by a user. The vocational mask includes a virtual retinal display, a memory device storing instructions, and a processing device communicatively coupled to the memory device and the virtual retinal display. The processing device executes the instructions to execute an artificial intelligence agent trained to perform at least one or more functions to determine certain information. The one or more functions include identifying perception-based objects and features, determining cognition-based scenery to identify one or more material defects, one or more assembly defects, one or more acceptable features, or some combination thereof, and determining one or more recommendations, instructions, or both. The processing device causes the certain information to be presented via the virtual retinal display.

30 Claims, 10 Drawing Sheets

10

(51) Int. Cl.

| | |
|---|---|
| *G06F 3/01* | (2006.01) |
| *G06T 11/60* | (2006.01) |
| *G06V 20/50* | (2022.01) |
| *G09G 3/00* | (2006.01) |
| *H04R 1/02* | (2006.01) |

(52) U.S. Cl.

CPC .............. *G06T 11/60* (2013.01); *G06V 20/50* (2022.01); *G09G 3/002* (2013.01); *H04R 1/028* (2013.01); *H04R 2499/15* (2013.01)

(56) References Cited

U.S. PATENT DOCUMENTS

| | | | |
|---|---|---|---|
| 8,428,926 | B2 | 4/2013 | Choquet |
| 9,641,569 | B2 | 5/2017 | Domke et al. |
| 9,684,303 | B2 | 6/2017 | Lamers et al. |
| 9,767,712 | B2 | 9/2017 | Postlethwaite et al. |
| 9,773,429 | B2 | 9/2017 | Boulware et al. |
| 9,786,193 | B2 | 10/2017 | Falash et al. |
| 9,836,987 | B2 | 12/2017 | Postlethwaite et al. |
| 9,881,520 | B2 | 1/2018 | Ullrich et al. |
| 9,922,236 | B2 | 3/2018 | Moore et al. |
| 9,939,234 | B1 | 4/2018 | Glauber |
| 9,965,973 | B2 | 5/2018 | Peters et al. |
| 9,994,228 | B2 | 6/2018 | Krueger |
| 10,012,962 | B2 | 7/2018 | Lamers et al. |
| 10,056,010 | B2 | 8/2018 | Salsich et al. |
| 10,688,589 | B2 | 6/2020 | Svendsen et al. |
| 11,633,539 | B1 | 4/2023 | Badik et al. |
| 11,733,667 | B2 | 8/2023 | Mehrotra et al. |
| 11,769,421 | B2 | 9/2023 | Wallace et al. |
| 11,769,423 | B2 | 9/2023 | Galasso et al. |
| 11,771,371 | B1 | 10/2023 | Lisy et al. |
| 11,783,724 | B1 | 10/2023 | Shubrick et al. |
| 11,783,727 | B1 | 10/2023 | Kelly et al. |
| 11,839,781 | B1 | 12/2023 | Dashevsky et al. |
| 2008/0038702 | A1 | 2/2008 | Choquet |
| 2009/0325131 | A1 | 12/2009 | Cernasov et al. |
| 2010/0271298 | A1 | 10/2010 | Vice et al. |
| 2011/0117527 | A1 | 5/2011 | Conrardy et al. |
| 2013/0194083 | A1 | 8/2013 | Rao et al. |
| 2014/0272839 | A1 | 9/2014 | Cutler |
| 2015/0170539 | A1 | 6/2015 | Chica et al. |
| 2015/0190887 | A1 | 7/2015 | Becker et al. |
| 2015/0260474 | A1 | 9/2015 | Rublowsky et al. |
| 2015/0375327 | A1 | 12/2015 | Becker et al. |
| 2016/0034764 | A1 | 2/2016 | Connor |
| 2016/0163221 | A1 | 6/2016 | Sommers et al. |
| 2016/0267806 | A1 | 9/2016 | Hsu et al. |
| 2017/0032281 | A1 | 2/2017 | Hsu |
| 2017/0150127 | A1 | 5/2017 | High et al. |
| 2017/0200394 | A1 | 7/2017 | Albrecht |
| 2017/0294140 | A1 | 10/2017 | Chica et al. |
| 2018/0126476 | A1 | 5/2018 | Meess et al. |
| 2018/0130376 | A1 | 5/2018 | Meess et al. |
| 2018/0180893 | A1 | 6/2018 | Gupta |
| 2018/0185110 | A1 | 7/2018 | Kumar et al. |
| 2018/0225993 | A1 | 8/2018 | Buras et al. |
| 2019/0076700 | A1 | 3/2019 | Quillin |
| 2019/0163274 | A1 | 5/2019 | Sun et al. |
| 2019/0340954 | A1 | 11/2019 | Schneider |
| 2019/0380792 | A1 | 12/2019 | Poltaretskyi et al. |
| 2020/0128348 | A1 | 4/2020 | Eronen et al. |
| 2020/0269065 | A1* | 8/2020 | Broeng ................. A61M 21/00 |
| 2020/0273365 | A1 | 8/2020 | Wallace et al. |
| 2020/0337407 | A1 | 10/2020 | Hsu |
| 2020/0349770 | A1* | 11/2020 | Kuehne ................. G06T 19/006 |
| 2020/0368904 | A1 | 11/2020 | Aldridge et al. |
| 2020/0371737 | A1 | 11/2020 | Leppänen et al. |
| 2021/0216773 | A1 | 7/2021 | Bohannon et al. |
| 2021/0343086 | A1 | 11/2021 | Long, III |
| 2022/0016776 | A1 | 1/2022 | Lonsberry et al. |
| 2022/0258268 | A1 | 8/2022 | Becker |
| 2022/0404819 | A1 | 12/2022 | Ba et al. |
| 2023/0129708 | A1 | 4/2023 | Stone et al. |
| 2023/0131469 | A1 | 4/2023 | Karaaslan et al. |
| 2023/0260415 | A1 | 8/2023 | Greunke |
| 2023/0270344 | A1 | 8/2023 | Leboeuf et al. |
| 2023/0343310 | A1 | 10/2023 | Seim et al. |
| 2023/0347186 | A1 | 11/2023 | Klatt et al. |
| 2024/0119345 | A1 | 4/2024 | Everman et al. |
| 2024/0207982 | A1 | 6/2024 | Becker et al. |
| 2025/0191485 | A1 | 6/2025 | Kravitz |

FOREIGN PATENT DOCUMENTS

| | | | |
|---|---|---|---|
| DE | 102020206308 | A1 | 11/2021 |
| EP | 0741346 | A2 | 11/1996 |
| EP | 2099588 | B1 | 10/2011 |
| EP | 3812105 | A1 | 4/2021 |
| EP | 3929894 | A1 | 12/2021 |
| EP | 3682393 | B1 | 12/2023 |
| JP | 2012520521 | A | 9/2012 |
| KR | 100934614 | B1 | 12/2009 |
| KR | 20150092444 | A | 8/2015 |
| WO | 2006131827 | A2 | 12/2006 |
| WO | 2015033152 | A2 | 3/2015 |
| WO | 2015195303 | A1 | 12/2015 |
| WO | 2017151778 | A1 | 9/2017 |
| WO | 2021229927 | A1 | 11/2021 |
| WO | 2022208595 | A1 | 10/2022 |
| WO | 2022266245 | A1 | 12/2022 |
| WO | 2023118877 | A1 | 6/2023 |

OTHER PUBLICATIONS

International Search Report and Written Opinion dtd Jun. 30, 2025 for PCT/US2025/025298, dtd Jun. 30, 2025, 20 pages.

International Search Report and Written Opinion dtd Jun. 30, 2025 for PCT/US2025/023118, dtd Jun. 30, 2025, 6 pages.

International Search Report dtd Jun. 30, 2025 for PCT/US2025/024263, dtd Jun. 30, 2025, 6 pages.

International Search Report and Written Opinion dtd Jun. 30, 2025 for PCT/US2025/023990, dtd Jun. 30, 2025, 11 pages.

International Search Report and Written Opinion dtd Jun. 30, 2025 for PCT/US2025/024512, dtd Jun. 30, 2025, 14 pages.

International Search Report and Written Opinion dtd Jun. 30, 2025 for PCT/US2025/025300, dtd Jun. 30, 2025, 21 pages.

Schume, Philipp, "Artificial Intelligence in Industrial Welding Produces Near-Real-Time Insights Through Virtually 100% Sample Sizes", AWS for Industries, published Oct. 26, 2023, available at: https://aws.amazon.com/blogs/industries/artificial-intelligence-in-industrial-welding-produces-near-real-time-insights-through-virtually-100-sample-sizes/p. 3.

Su, Yun-Peng et al., "Integrating Virtual, Mixed, and Augmented Reality into Remote Robotic Applications: A Brief Review of Extended Reality-Enhanced Robotic Systems for Intuitive Telemanipulation and Telemanufacturing Tasks in Hazardous Conditions", Appl. Sci. 2023, 13, 12129, https://doi.org/10.3390/app132212129, https://www.mdpi.com.

Gonzalez, Claudia et al., Advanced Teleoperation and Control System for Industrial Robots Baased on Augmented Virtuality and Haptic Feedback, Journal of Manufacturing Systems, vol. 59, pp. 283-298, published Apr. 30, 2021.

Wang, Q. et al., "Modeling of Human Welders' Operations in Virtual Reality Human-Robot Interaction", IEEE Robotics and Automation Letters, vol. 4, Issue 3, published Jun. 10, 2019, available at: https://ieeexplore.ieee.org/abstract/document/8733861.com.

Johnson, Tate et al., "Augmenting Welding Training: an XR Platform to Foster Muscle Memory and Mindfulness for Skills Development", ISS Companion '23: Companion Proceedings of the 2023 Conference on Interactive Surfaces and Spaces, pp. 61-64, published Nov. 5, 2023, available at: https://dl.acm.org/doi/10.1145/3626485.3626544.com.

Chan, Vei Siang et al., "VR and AR Virtual Welding for Psychomotor Skills: A Systematic Review", Multimedia Tools and Applications, vol. 81, pp. 12459-12493, published Feb. 19, 2022, available at: https://link.springer.com/article/10.1007/s11042-022-12293-5.com.

(56)               References Cited

OTHER PUBLICATIONS

Y. Wang, Y. Chen, Z. Nan and Y. Hu, "Study on Welder Training by Means of Haptic Guidance and Virtual Reality for Arc Welding," 2006 IEEE International Conference on Robotics and Biomimetics, Kunming, China, 2006, pp. 954-958, doi: 10.1109/ROBIO.2006. 340349.
International Search Report and Written Opinion for PCT/US2025/ 026401 dated Aug. 22, 2025, 18 pages.

* cited by examiner

10

116

Cloud-Based Computing System

128
Server

129
Database

152
Training Engine

154
Machine Learning Model(s)

20
Network

130
Vocational Mask

132.2
Edge Processor

134
Peripheral Haptic Device

136
Tool

140
Computing Device

142
User Interface 132.1
Edge Processor

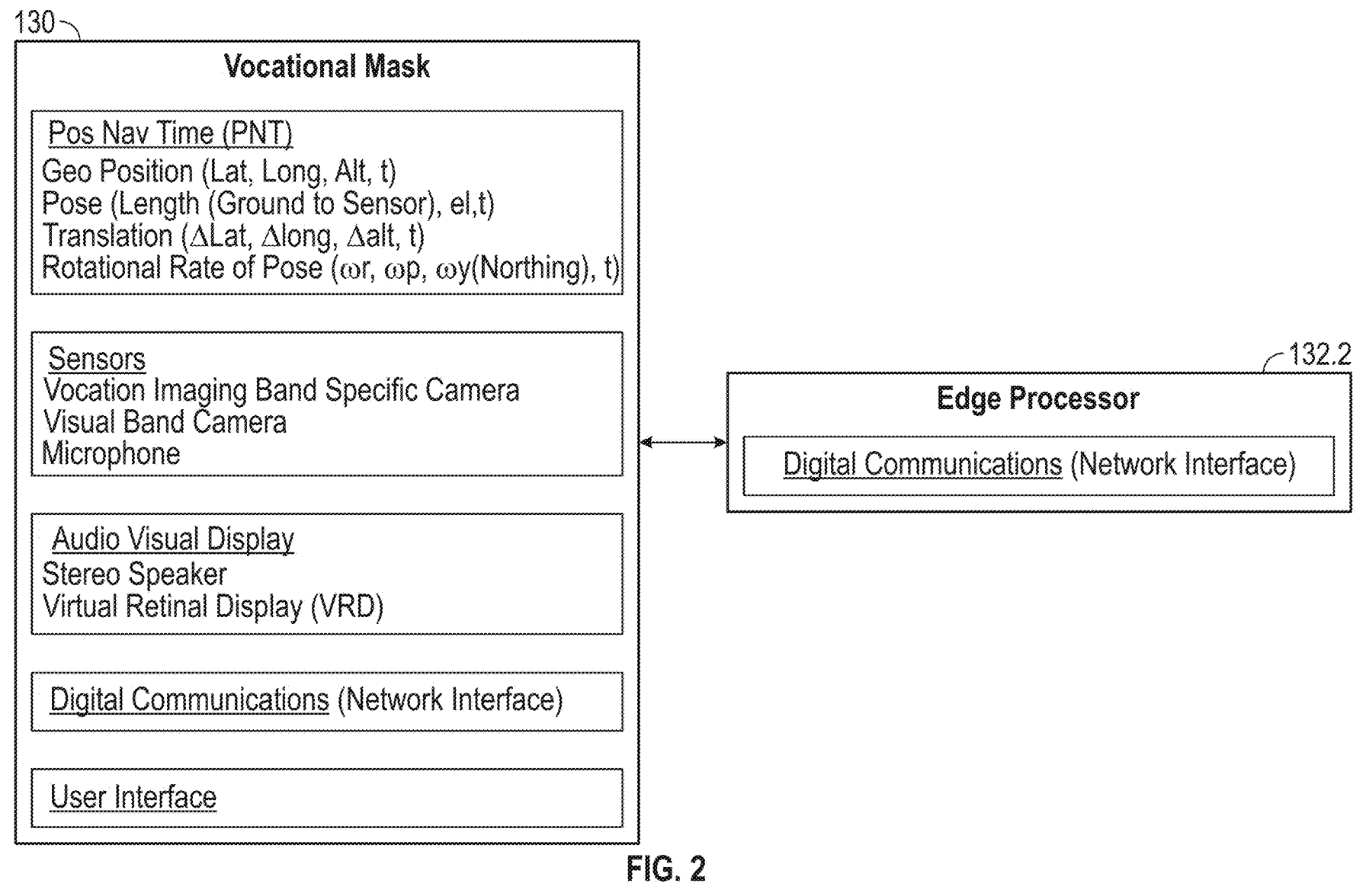

Edge Processor

Digital Communications (Network Interface)

132.2

Vocational Mask

130

Pos Nav Time (PNT)
Geo Position (Lat, Long, Alt, t)
Pose (Length (Ground to Sensor), el,t)
Translation (ΔLat, Δlong, Δalt, t)
Rotational Rate of Pose (ωr, ωp, ωy(Northing), t)

Sensors
Vocation Imaging Band Specific Camera
Visual Band Camera
Microphone

Audio Visual Display
Stereo Speaker
Virtual Retinal Display (VRD)

Digital Communications (Network Interface)

User Interface

FIG. 2

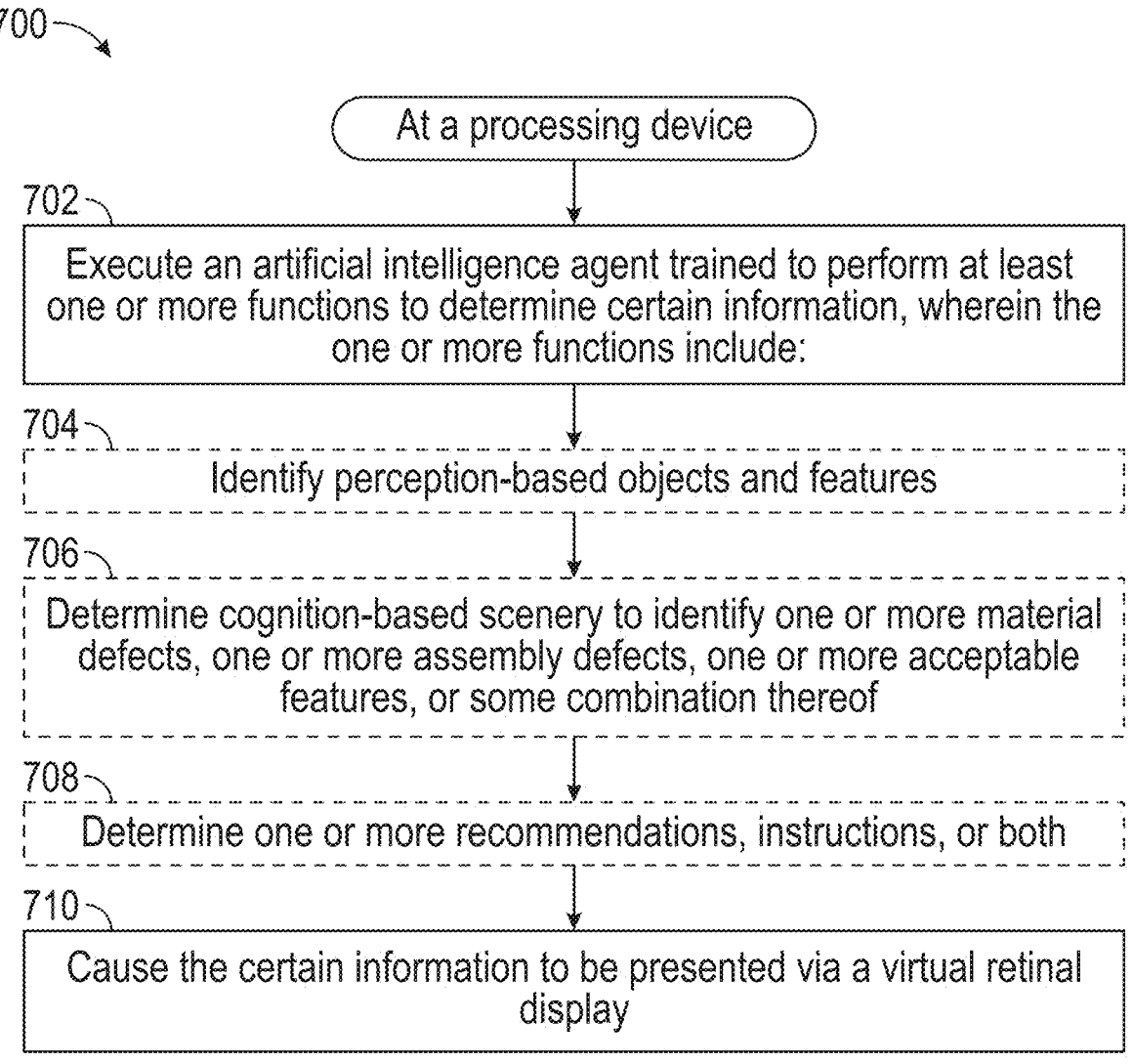

700

At a processing device

702

Execute an artificial intelligence agent trained to perform at least one or more functions to determine certain information, wherein the one or more functions include:

704

Identify perception-based objects and features

706

Determine cognition-based scenery to identify one or more material defects, one or more assembly defects, one or more acceptable features, or some combination thereof

708

Determine one or more recommendations, instructions, or both

710

Cause the certain information to be presented via a virtual retinal display

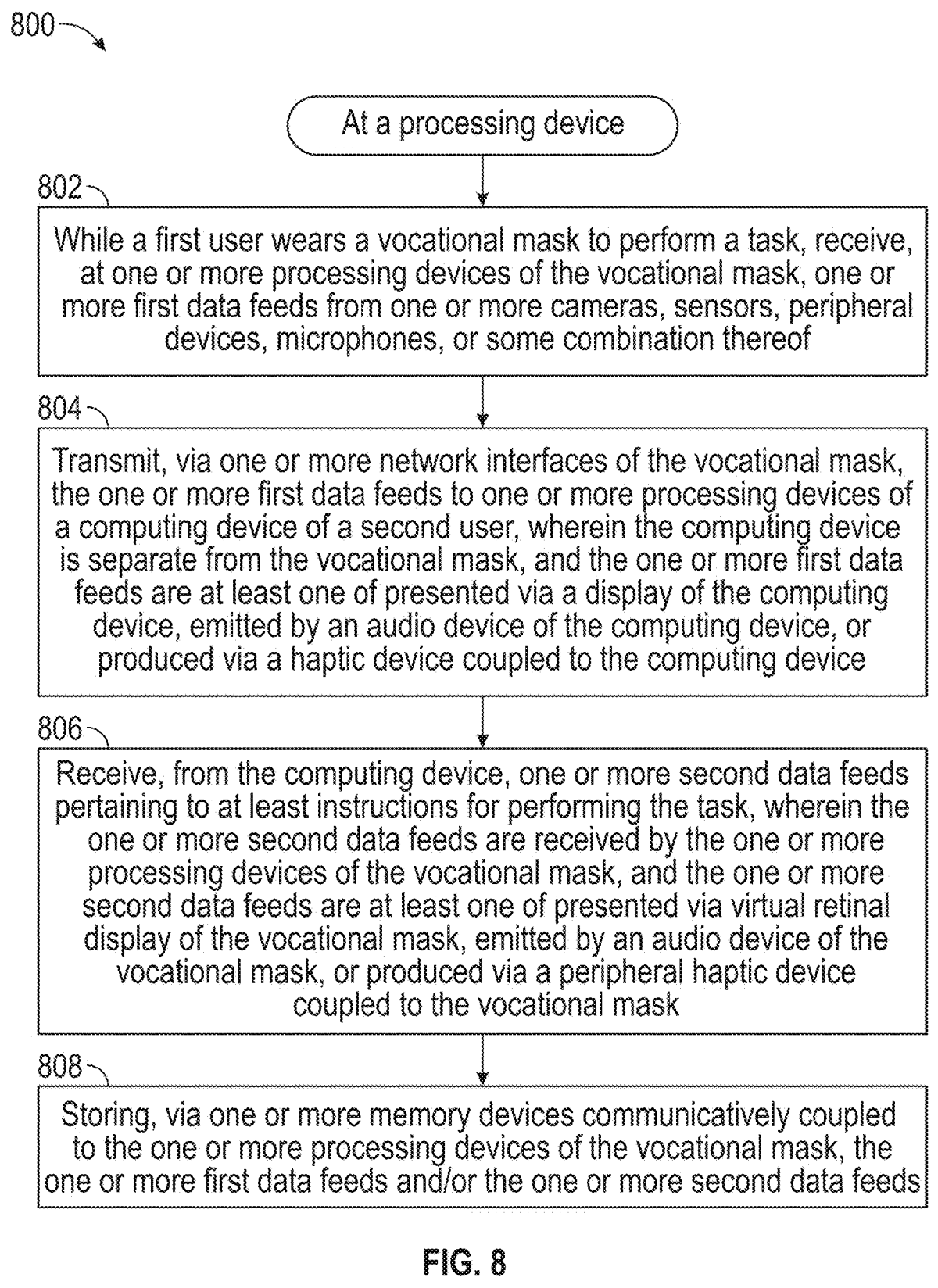

At a processing device

802 —⟍

While a first user wears a vocational mask to perform a task, receive, at one or more processing devices of the vocational mask, one or more first data feeds from one or more cameras, sensors, peripheral devices, microphones, or some combination thereof

804 —⟍

Transmit, via one or more network interfaces of the vocational mask, the one or more first data feeds to one or more processing devices of a computing device of a second user, wherein the computing device is separate from the vocational mask, and the one or more first data feeds are at least one of presented via a display of the computing device, emitted by an audio device of the computing device, or produced via a haptic device coupled to the computing device

806 —⟍

Receive, from the computing device, one or more second data feeds pertaining to at least instructions for performing the task, wherein the one or more second data feeds are received by the one or more processing devices of the vocational mask, and the one or more second data feeds are at least one of presented via virtual retinal display of the vocational mask, emitted by an audio device of the vocational mask, or produced via a peripheral haptic device coupled to the vocational mask

808 —⟍

Storing, via one or more memory devices communicatively coupled to the one or more processing devices of the vocational mask, the one or more first data feeds and/or the one or more second data feeds

FIG. 8

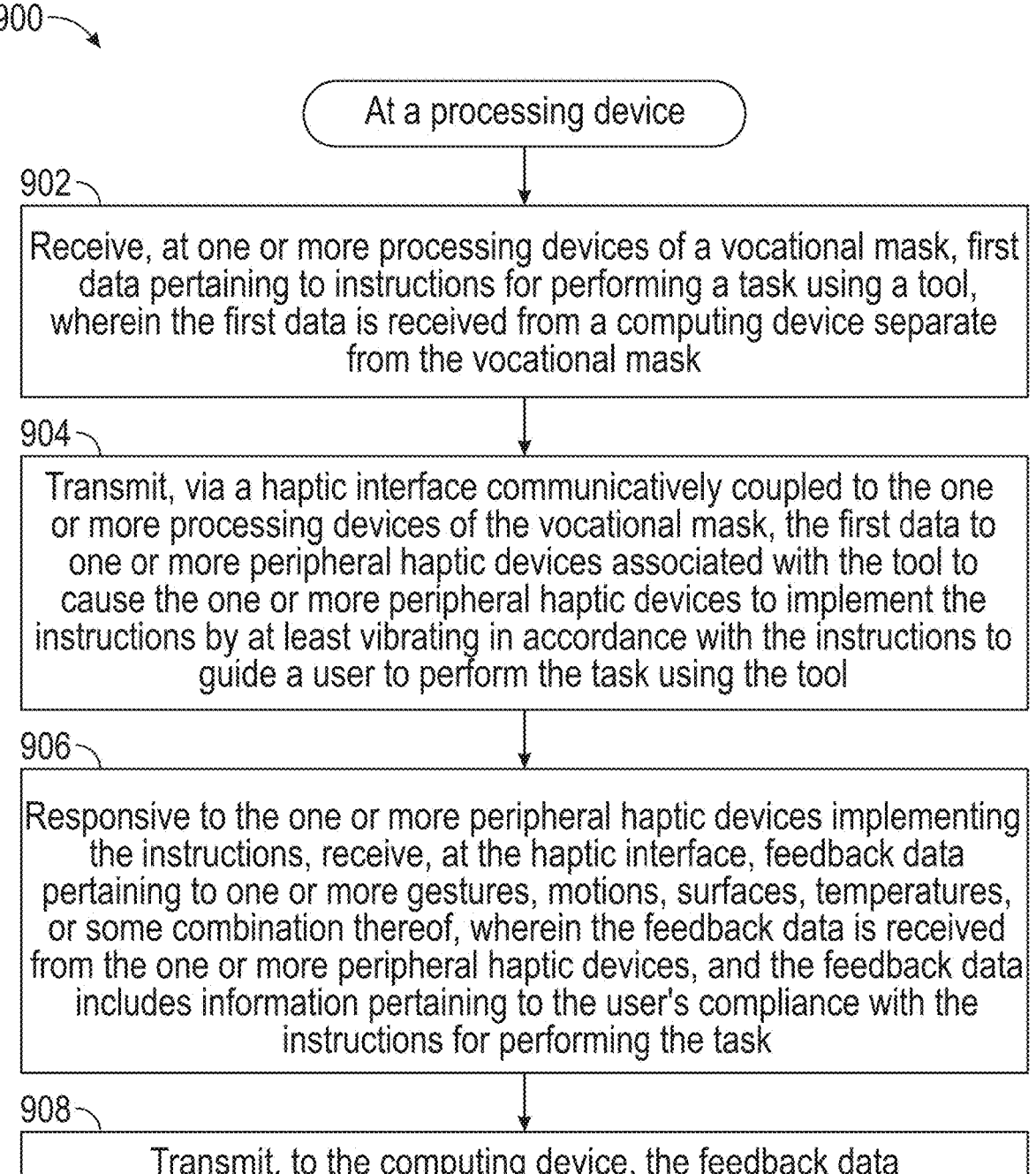

900

At a processing device

902

Receive, at one or more processing devices of a vocational mask, first data pertaining to instructions for performing a task using a tool, wherein the first data is received from a computing device separate from the vocational mask

904

Transmit, via a haptic interface communicatively coupled to the one or more processing devices of the vocational mask, the first data to one or more peripheral haptic devices associated with the tool to cause the one or more peripheral haptic devices to implement the instructions by at least vibrating in accordance with the instructions to guide a user to perform the task using the tool

906

Responsive to the one or more peripheral haptic devices implementing the instructions, receive, at the haptic interface, feedback data pertaining to one or more gestures, motions, surfaces, temperatures, or some combination thereof, wherein the feedback data is received from the one or more peripheral haptic devices, and the feedback data includes information pertaining to the user's compliance with the instructions for performing the task

908

Transmit, to the computing device, the feedback data

FIG. 9

SYSTEMS AND METHODS FOR USING A VOCATIONAL MASK WITH A HYPER-ENABLED WORKER

CROSS-REFERENCES TO RELATED APPLICATIONS

This application claims priority to U.S. Application Patent Ser. No. 63/607,354 filed Dec. 7, 2023, titled "SYSTEMS AND METHODS FOR USING A VOCATIONAL MASK WITH A HYPER-ENABLED WORKER," the entire disclosure of which is hereby incorporated by reference for all purposes.

TECHNICAL FIELD

This disclosure relates to enabling workers to perform vocations. More specifically, this disclosure relates to systems and methods for using a vocational mask with a hyper-enabled worker.

BACKGROUND

People use various tools and/or equipment to perform various vocations. For example, a welder may use a welding mask and/or a welding gun to weld an object. The welder may participate in training courses prior to welding the object. A master welder may lead the training courses to train the welder how to properly weld. In some instances, the master welder may be located at a physical location that is remote from where a student welder is physically located.

SUMMARY

In one embodiment, a system includes a vocational mask configured to be worn by a user. The vocational mask includes a virtual retinal display, a memory device storing instructions, and a processing device communicatively coupled to the memory device and the virtual retinal display. The processing device executes the instructions to execute an artificial intelligence agent trained to perform at least one or more functions to determine certain information. The one or more functions include identifying perception-based objects and features, determining cognition-based scenery to identify one or more material defects, one or more assembly defects, one or more acceptable features, or some combination thereof, and determining one or more recommendations, instructions, or both. The processing device causes the certain information to be presented via the virtual retinal display.

In one embodiment, a system may include goggles configured to be worn by a user. The goggles may includes a display, a memory device storing instructions, and a processing device communicatively coupled to the memory device and the display. The processing device executes the instructions to execute an artificial intelligence agent trained to perform at least one or more functions to determine certain information. The one or more functions include identifying perception-based objects and features, determining cognition-based scenery to identify one or more material defects, one or more assembly defects, one or more acceptable features, or some combination thereof, and determining one or more recommendations, instructions, or both. The process device causes the certain information to be presented via the display.

In one embodiment, a system may include a monocular welding goggle configured to be worn by a user. The monocular welding goggle may include a display, a memory device storing instructions, and a processing device communicatively coupled to the memory device and the display. The processing device executes the instructions to execute an artificial intelligence agent trained to perform at least one or more functions to determine certain information. The one or more functions include identifying perception-based objects and features, determining cognition-based scenery to identify one or more material defects, one or more assembly defects, one or more acceptable features, or some combination thereof, and determining one or more recommendations, instructions, or both. The process device causes the certain information to be presented via the display.

In one embodiment, a computer-implemented method may include, while a first user wears a vocational mask to perform a task, receiving, at one or more processing devices of the vocational mask, one or more first data feeds from one or more cameras, sensors, peripheral haptic devices, microphones, or some combination thereof. The method may include transmitting, via one or more network interfaces of the vocational mask, the one or more first data feeds to one or more processing devices of a computing device of a second user, wherein the computing device is separate from the vocational mask, and the one or more first data feeds are at least one of presented via a display of the computing device, emitted by an audio device of the computing device, or produced via a haptic device coupled to the computing device. The method may include receiving, from the computing device, one or more second data feeds pertaining to at least instructions for performing the task, wherein the one or more second data feeds are received by the one or more processing devices of the vocational mask, and the one or more second data feeds are at least one of presented via a virtual retinal display of the vocational mask, emitted by an audio device of the vocational mask, or produced via a peripheral haptic device coupled to the vocational mask. The method may include storing, via one or more memory devices communicatively coupled to the one or more processing devices of the vocational mask, the one or more first data feeds and/or the one or more second data feeds.

In one embodiment, a computer-implemented method includes receiving, at one or more processing devices of a vocational mask, first data pertaining to instructions for performing a task using a tool, wherein the first data is received from a computing device separate from the vocational mask. The method includes transmitting, via a haptic interface communicatively coupled to the one or more processing devices of the vocational mask, the first data to one or more peripheral haptic devices associated with the tool to cause the one or more peripheral haptic devices to implement the instructions by at least vibrating in accordance with the instructions to guide a user to perform the task using the tool. That is, the first data may include one or more control instructions that control operation of the one or more peripheral haptic devices. The method includes responsive to the one or more peripheral haptic devices implementing the instructions, receiving feedback data pertaining to one or more gestures, motions, surfaces, temperatures, or some combination thereof, wherein the feedback data is received from the one or more peripheral haptic devices, and the feedback data comprises information pertaining to the user's compliance with the instructions for performing the task. The method includes transmitting, to the computing device, the feedback data.

In one embodiment, a tangible, non-transitory computer-readable medium stores instructions that, when executed, cause a processing device to perform any operation of any method disclosed herein.

In one embodiment, a system includes a memory device storing instructions and a processing device communicatively coupled to the memory device. The processing device executes the instructions to perform any operation of any method disclosed herein.

Other technical features may be readily apparent to one skilled in the art from the following figures, descriptions, and claims.

BRIEF DESCRIPTION OF THE DRAWINGS

For a detailed description of example embodiments, reference will now be made to the accompanying drawings in which:

FIG. 2 illustrates a component diagram for a vocational mask according to certain embodiments of this disclosure;

FIG. 7 illustrates an example of a method for executing an artificial intelligence agent to determine certain information projected via a vocational mask of a user according to certain embodiments of this disclosure;

FIG. 8 illustrates an example of a method for transmitting instructions for performing a task via bidirectional communication between a vocational mask and a computing device according to certain embodiments of this disclosure;

FIG. 9 illustrates an example of a method for implementing instructions for performing a task using a peripheral haptic device according to certain embodiments of this disclosure.

NOTATION AND NOMENCLATURE

Figure 1:
FIG. 1 illustrates a system architecture according to certain embodiments of this disclosure.

Various terms are used to refer to particular system components. Different entities may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer or section from another region, layer or section. Terms such as "first," "second," and other numerical terms, when used herein, do not imply a sequence or order unless clearly indicated by the context. Thus, a first element, component, region, layer or section discussed below could be termed a second element, component, region, layer or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), solid state drives (SSDs), flash memory, or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

DETAILED DESCRIPTION

The following discussion is directed to various embodiments of the disclosed subject matter. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

FIGS. 1 through 10 discussed below, and the various embodiments used to describe the principles of this disclosure in this patent document are by way of illustration only and should not be construed in any way to limit the scope of the disclosure.

Some of the disclosed embodiments relate to one or more artificial intelligent enhanced vocational tools for workers to use to perform a job, task, and/or vocation. In some embodiments, the vocational tools may be in the form of a vocational mask that projects work instructions using imagery, animation, video, text, audio, and the like. The vocational tools may be used by workers to enhance the efficiency and proficiency of performing professional and vocational tasks, such as but not limited to supply chain operations, manufacturing and warehousing processes, product inspection, coworker and master-apprentice bidirectional collaboration and communication with or without haptic sensory feedback, other telepresence, and the like.

Some of the disclosed embodiments may be used to collect data, metadata, and multiband video to aid in product acceptance, qualification, and full lifecycle product management. Further, some of the disclosed embodiments may aid a failure reporting, analysis, and corrective action system, a failure mode, effects, and criticality analysis system, other sustainment and support activities and tasks to accommodate worker dislocation and multi-decade lifecycle of some products.

In one embodiment, a vocational mask is disclosed that employs bidirectional communication to include voice and imagery and still and audio video imagery recording with other colleagues over a distance. The vocational mask may provide virtual images of objects to a person wearing the vocational mask via a display (e.g., virtual retinal display). The vocational mask may enable bidirectional communications with collaborators and/or students. Further, the vocational mask may enable bidirectional audio, visual, and haptic communication to provide a master-apprentice relationship. The vocational mask may include multiple electromagnetic spectrum and acoustic sensors/imagers. The vocational mask may also provide multiband audio and video sensed imagery to a wearer of the vocational mask.

The vocational mask may be configured to provide display capabilities to project images onto one or more irises of the wearer to display alphanumeric data and graphic/animated work instructions, for example. The vocational mask may also include one or more speakers to emit audio related to work instructions, such as those provided by a master trained user, supervisor, collaborator, teacher, etc.

The vocational mask may include an edge-based processor that executes an artificial intelligence agent. The artificial intelligence agent may be implemented in computer instructions stored on one or more memory devices and executed by one or more processing devices. The artificial intelligence agent may be trained to perform one or more functions, such as but not limited to (i) perception-based object and feature identification, (ii) cognition-based scenery understanding, to identify material and assembly defects versus acceptable features, and (iii) decision making to aid the wearer and to provide relevant advice and instruction in real-time or near real-time to the wearer of the vocational mask. The data that is collected may be used for inspection and future analyses of product quality, product design, and the like. Further, the collected data may be stored for instructional analyses and providing lessons, mentoring, collaboration, and the like.

The vocational mask may include one or more components (e.g., processing device, memory device, display, etc.), interfaces, and/or sensors configured to provide sensing capabilities to understand hand motions and use of a virtual user interface (e.g., keyboards) and other haptic instructions. The vocational mask may include a haptic interface to allow physical bidirectional haptic sensing and stimulation via the bidirectional communications to other users and/or collaborators using a peripheral haptic device (e.g., a welding gun).

In some embodiments, the vocational mask may be in the form of binocular goggles, monocular googles, finishing process glasses (e.g., grind, chamfer, debur, sand polish, coat, etc.), or the like. The vocational mask may be attached to a welding helmet. The vocational mask may include an optical bench that aligns a virtual retinal display to one or more eyes of a user. The vocational mask may include a liquid crystal display welding helmet, a welding camera, an augmented reality/virtual reality headset, etc.

The vocational mask may augment projections by providing augmented reality cues and information to assist a worker (e.g., welder) with contextual information, which may include setup, quality control, procedures, training, and the like. Further, the vocational mask may provide a continuum of visibility from visible spectrum (arc off) through high-intensity/ultraviolet (arc on). Further, some embodiments include remote feedback and recording of images and bidirectional communications to a trainer, supervisor, mentor, master user, teacher, collaborator, etc. who can provide visual, auditory, and/or haptic feedback to the wearer of the vocational mask in real-time or near real-time.

In some embodiments, the vocational mask may be integrated with a welding helmet. In some embodiments, the vocational mask may be a set of augmented reality/virtual reality goggles worn under a welding helmet (e.g., with external devices, sensors, cameras, etc. appended for image/data gathering). In some embodiments, the vocational mask may be a set of binocular welding goggles or a monocular welding goggle to be worn under or in lieu of a welding helmet (e.g., with external devices, sensors, cameras, etc. appended to the googles for image/data gathering). In some embodiments, the vocational mask may include a mid-band or long wave context camera displayed to the user and monitor.

In some embodiments, information may be superpositioned or superimposed onto a display without the user (e.g., worker, student, etc.) wearing a vocational mask. The information may include work instructions in the form of text, images, alphanumeric characters, video, etc. The vocational mask may function across both visible light (arc off) and high intensity ultraviolet light (arc on) conditions. The vocational mask may natively or in conjunction with other personal protective equipment provide protection against welding flash. The vocational mask may enable real-time or near real-time two-way communication with a remote instructor or supervisor. The vocational mask may provide one or more video, audio, and data feeds to a remote instructor or supervisor. The vocational mask and/or other components in a system may enable recording of all data and communications. The system may provide a mechanism for replaying the data and communications, via a media player, for training purposes, quality control purposes, inspection purposes, and the like. The vocational mask and/or other components in a system may provide a mechanism for visual feedback from a remote instructor or supervisor. The vocational mask and/or other components in a system may provide a bidirectional mechanism for haptic feedback from a remote instructor or supervisor.

Further, the system may include an artificial intelligence simulation generator that generates task simulations to be transmitted to and presented via the vocational mask. The simulation of a task may be transmitted as virtual reality data to the vocational mask which includes a virtual reality headset and/or display to playback the virtual reality data. The virtual reality data may be configured based on parameters of a physical space in which the vocational mask is located, based on parameters of an object to be worked on, based on parameters of a tool to be used, and the like.

Turning now to the figures, FIG. 1 depicts a system architecture 10 according to some embodiments. The system architecture 10 may include one or more computing devices 140, one or more vocational masks 130, one or more peripheral haptic devices 134, and/or one or more tools 136 communicatively coupled to a cloud-based computing system 116. Each of the computing devices 140, vocational masks 130, peripheral haptic devices 134, tools 136, and components included in the cloud-based computing system 116 may include one or more processing devices, memory devices, and/or network interface cards. The network interface cards may enable communication via a wireless protocol for transmitting data over short distances, such as Bluetooth, ZigBee, NFC, etc. Additionally, the network interface cards may enable communicating data over long distances, and in one example, the computing devices 140, the vocational masks 130, the peripheral haptic devices 134, the tools 136, and the cloud-based computing system 116 may communicate with a network 20. Network 20 may be a public network (e.g., connected to the Internet via wired (Ethernet) or wireless (WiFi)), a private network (e.g., a local area network (LAN) or wide area network (WAN)), or a combination thereof. Network 20 may also include a node or nodes on the Internet of Things (IoT). The network 20 may be a cellular network.

The computing devices 140 may be any suitable computing device, such as a laptop, tablet, smartphone, smartwatch, ear buds, server, or computer. In some embodiments, the computing device 140 may be a vocational mask. The computing devices 140 may include a display capable of presenting a user interface 142 of an application. In some embodiments, the display may be a laptop display, smartphone display, computer display, tablet display, a virtual retinal display, etc. The application may be implemented in computer instructions stored on the one or more memory devices of the computing devices 140 and executable by the one or more processing devices of the computing device 140. The application may present various screens to a user. For example, the user interface 140 may present a screen that plays video received from the vocational mask 130. The video may present real-time or near real-time footage of what the vocational mask 130 is viewing, and in some instances, that may include a user's hands holding the tool 136 to perform a task (e.g., weld, sand, polish, chamfer, debur, paint, play a video game, etc.). Additional screens may be presented via the user interface 160.

In some embodiments, the application (e.g., website) executes within another application (e.g., web browser). The computing device 140 may also include instructions stored on the one or more memory devices that, when executed by the one or more processing devices of the computing devices 140 perform operations of any of the methods described herein.

In some embodiments, the computing devices 140 may include an edge processor 132.1 that performs one or more operations of any of the methods described herein. The edge processor 132.1 may execute an artificial intelligence agent to perform various operations described herein. The artificial intelligence agent may include one or more machine learning models that are trained via the cloud-based computing system 116 as described herein. The edge processor 132.1 may represent one or more general-purpose processing devices such as a microprocessor, central processing unit, or the like. More particularly, the edge processor 132.1 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The edge processor 132.1 may also be one or more special-purpose processing devices such as an application specific integrated circuit (ASIC), a field programmable gate array (FPGA), a digital signal processor (DSP), network processor, or the like.

In some embodiments, the vocational mask 130 may be attached to or integrated with a welding helmet, binocular goggles, a monocular goggle, glasses, a hat, a helmet, a virtual reality headset, a headset, a facemask, or the like. The vocational mask 130 may include various components as described herein, such as an edge processor 132.2. In some embodiments, the edge processor 132.2 may be located separately from the vocational mask 130 and may be included in another computing device, such as a server, laptop, desktop, tablet, smartphone, etc. The edge processor 132.2 may represent one or more general-purpose processing devices such as a microprocessor, central processing unit, or the like. More particularly, the edge processor 132.2 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The edge processor 132.2 may also be one or more special-purpose processing devices such as an application specific integrated circuit (ASIC), a field programmable gate array (FPGA), a digital signal processor (DSP), network processor, or the like.

The edge processor 132.2 may perform one or more operations of any of the methods described herein. The edge processor 132.2 may execute an artificial intelligence agent to perform various operations described herein. The artificial intelligence agent may include one or more machine learning models that are trained via the cloud-based computing system 116 as described herein. For example, the cloud-based computing system 116 may train one or more machine learning models 154 via a training engine 152, and may transmit the parameters used to train the machine learning model to the edge processor 132.2 such that the edge processor 132.2 can implement the parameters in the machine learning models executing locally on the vocational mask 130 or computing device 140.

The edge processor 132.2 may include a data concentrator that collects data from multiple vocational masks 130 and transmits the data to the cloud-based computing system 116. The data concentrator may map information to reduce bandwidth transmission costs of transmitting data. In some embodiments, a network connection may not be needed for the edge processor 132.2 to collect data from vocational masks and to perform various functions using the trained machine learning models 154.

The vocational mask 130 may also include a network interface card that enables bidirectional communication with any other computing device 140, such as other vocational masks 130, smartphones, laptops, desktops, servers, wearable devices, tablets, etc. The vocational mask 130 may also be communicatively coupled to the cloud-based computing system 116 and may transmit and receive information and/or data to and from the cloud-based computing system 116. The vocational mask 130 may include various sensors, such as position sensors, acoustic sensors, haptic sensors, microphones, temperature sensors, accelerometers, and the like. The vocational mask 130 may include various cameras configured to capture audio and video. The vocational mask 130 may include a speaker to emit audio. The vocational mask 130 may include a haptic interface configured to transmit and receive haptic data to and from the peripheral haptic device 134. The haptic interface may be communicatively coupled to a processing device (e.g., edge processor 132.2) of the vocational mask 130.

In some embodiments, the peripheral haptic device 134 may be attached to or integrated with the tool 136. In some embodiments, the peripheral haptic device 134 may be separate from the tool 136. The peripheral haptic device 134 may include one or more haptic sensors that provide force, vibration, touch, and/or motion sensations to the user, among other things. The peripheral haptic device 134 may be used to enable a person remote from a user of the peripheral haptic device 134 to provide haptic instructions to perform a task (e.g., weld, shine, polish, paint, control a video game controller, grind, chamfer, debur, etc.). The peripheral haptic device 134 may include one or more processing devices, memory devices, network interface cards, haptic interfaces, etc. In some embodiments, the peripheral haptic device 134 may be communicatively coupled to the vocational mask 130, the computing device 140, and/or the cloud-based computing system 116.

The tool 136 may be any suitable tool, such as a welding gun, a video game controller, a paint brush, a pen, a utensil, a grinder, a sander, a polisher, a gardening tool, a yard tool, a glove, or the like. The tool 136 may be handheld such that the peripheral haptic device 134 is enabled to provide haptic instructions for performing a task to the user holding the tool 136. In some embodiments, the tool 136 may be wearable by the user. The tool 136 may be used to perform a task. In some embodiments, the tool 136 may be located in a physical proximity to the user in a physical space.

In some embodiments, the cloud-based computing system 116 may include one or more servers 128 that form a distributed computing architecture. The servers 128 may be a rackmount server, a router computer, a personal computer, a portable digital assistant, a mobile phone, a laptop computer, a tablet computer, a camera, a video camera, a netbook, a desktop computer, a media center, any other device capable of functioning as a server, or any combination of the above. Each of the servers 128 may include one or more processing devices, memory devices, data storage, and/or network interface cards. The servers 128 may be in communication with one another via any suitable communication protocol. The servers 128 may execute an artificial intelligence (AI) engine and/or an AI agent that uses one or more machine learning models 154 to perform at least one of the embodiments disclosed herein. The cloud-based computing system 116 may also include a database 129 that stores data, knowledge, and data structures used to perform various embodiments. For example, the database 129 may store multimedia data of users performing tasks using tools, communications between vocational masks 130 and/or computing devices 140, virtual reality simulations, augmented reality information, recommendations, instructions, and the like. The database 129 may also store user profiles including characteristics particular to each user. In some embodiments, the database 129 may be hosted on one or more of the servers 128.

In some embodiments the cloud-based computing system 116 may include a training engine 152 capable of generating the one or more machine learning models 154. The machine learning models 154 may be trained to identify perception-based objects and features using training data that includes labeled inputs of images including certain objects and features mapped to labeled outputs of identities or characterizations of those objects and features. The machine learning models 154 may be trained determine cognition-based scenery to identify one or more material defects, one or more assembly defects, one or more acceptable features, or some combination thereof using training data that includes labeled input of scenery images of objects including material defects, assembly defects, and/or acceptable features mapped to labeled outputs that characterize and/or identify the material defects, assembly defects, and/or acceptable features. The machine learning models 154 may be trained to determine one or more recommendations, instructions, or both using training data including labeled input of images (e.g., objects, products, tools, actions, etc.) and tasks to be performed (e.g., weld, grind, chamfer, debur, sand, polish, coat, etc.) mapped to labeled outputs including recommendations, instructions, or both.

The one or more machine learning models 154 may be generated by the training engine 152 and may be implemented in computer instructions executable by one or more processing devices of the training engine 152 and/or the servers 128. To generate the one or more machine learning models 154, the training engine 152 may train the one or more machine learning models 154. The one or more machine learning models 154 may also be executed by the edge processor 132 (132.1, 132.2). The parameters used to train the one or more machine learning models 154 by the training engine 12 at the cloud-based computing system 116 may be transmitted to the edge processor 132 (132.1, 132.2) to be implemented locally at the vocational mask 130 and/or the computing device 140.

The training engine 152 may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine 152 may be cloud-based, be a real-time software platform, include privacy software or protocols, and/or include security software or protocols. To generate the one or more machine learning models 154, the training engine 152 may train the one or more machine learning models 154.

The one or more machine learning models 154 may refer to model artifacts created by the training engine 152 using training data that includes training inputs and corresponding target outputs. The training engine 152 may find patterns in the training data wherein such patterns map the training input to the target output and generate the machine learning models 154 that capture these patterns. Although depicted separately from the server 128, in some embodiments, the training engine 152 may reside on server 128. Further, in some embodiments, the database 129, and/or the training engine 152 may reside on the computing devices 12.

As described in more detail below, the one or more machine learning models 154 may comprise, e.g., a single level of linear or non-linear operations (e.g., a support vector machine [SVM]) or the machine learning models 154 may be a deep network, i.e., a machine learning model comprising multiple levels of non-linear operations. Examples of deep networks are neural networks, including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

FIG. 2 illustrates a component diagram for a vocational mask 130 according to certain embodiments of this disclosure. The edge processor 132.2 is also depicted. In some embodiments, the edge processor 132.2 may be included in a computing device separate from the vocational mask 130, and in some embodiments, the edge processor 132.2 may be included in the vocational mask 130.

The vocational mask 130 may include various position, navigation, and time (PNT) components, sensors, and/or devices that enable determining the geographical positon (latitude, longitude, altitude, time), pose (length (ground to sensor), elevation, time), translation (delta in latitude, delta in longitude, delta in altitude, time), the rotational rate of pose, and the like.

In some embodiments, the vocational mask 130 may include one or more sensors, such as vocation imaging band specific cameras, visual band cameras, microphones, and the like.

In some embodiments, the vocational mask 130 may include an audio visual display, such as a stereo speaker, a virtual retinal display, a liquid crystal display, a virtual reality headset, and the like. A virtual retinal display may be a retinal scan display or retinal projector that draws a raster display directly onto the retina of the eye. In some embodiments, the virtual retinal display may include drive electronics that transmit data to a photon generator and/or intensity modulator. These components may process the data (e.g., video, audio, haptic, etc.) and transmit the processed data to a beam scanning component that further transmits data to an optical projector that projects an image and/or video to a retina of a user.

In some embodiments, the vocational mask 130 may include a network interface card that enables bidirectional communication (digital communication) with other vocational masks and/or computing device 140.

In some embodiments, the vocational mask 130 may provide a user interface to the user via the display described herein.

In some embodiments, the edge processor 132.2 may include a network interface card that enables digital communication with the vocational mask 130, the computing device 140, the cloud-based computing system 116, or the like.

Figure 3:
FIG. 3 illustrates bidirectional communication between communicatively coupled vocational masks according to certain embodiments of this disclosure.

FIG. 3 illustrates bidirectional communication between communicatively coupled vocational masks 130 according to certain embodiments of this disclosure. As depicted, a user 306 is wearing a vocational mask 130. In the depicted example, the vocational mask 130 is attached to or integrated with a welding helmet 308. The user is viewing an object 300. The vocational mask 130 may include multiple electromagnetic spectrum and/or acoustic sensors/imagers 304 to enable obtaining audio, video, acoustic, etc. data while observing the object 300 and/or performing a task (e.g., welding).

Further, as depicted, the vocational mask 130 may be communicatively coupled to one or more other vocational masks worn by other users and may communicate data in real-time or near real-time such that bidirectional audio visual and haptic communications fosters a master-apprentice relationship. In some embodiments, the bidirectional communication enabled by the vocational masks 130 may enable collaboration between a teacher or collaborator and students. Each of the users wearing the vocational mask 130 may be enabled to visualize the object 300 that the user is viewing in real-time or near real-time.

Figure 4:
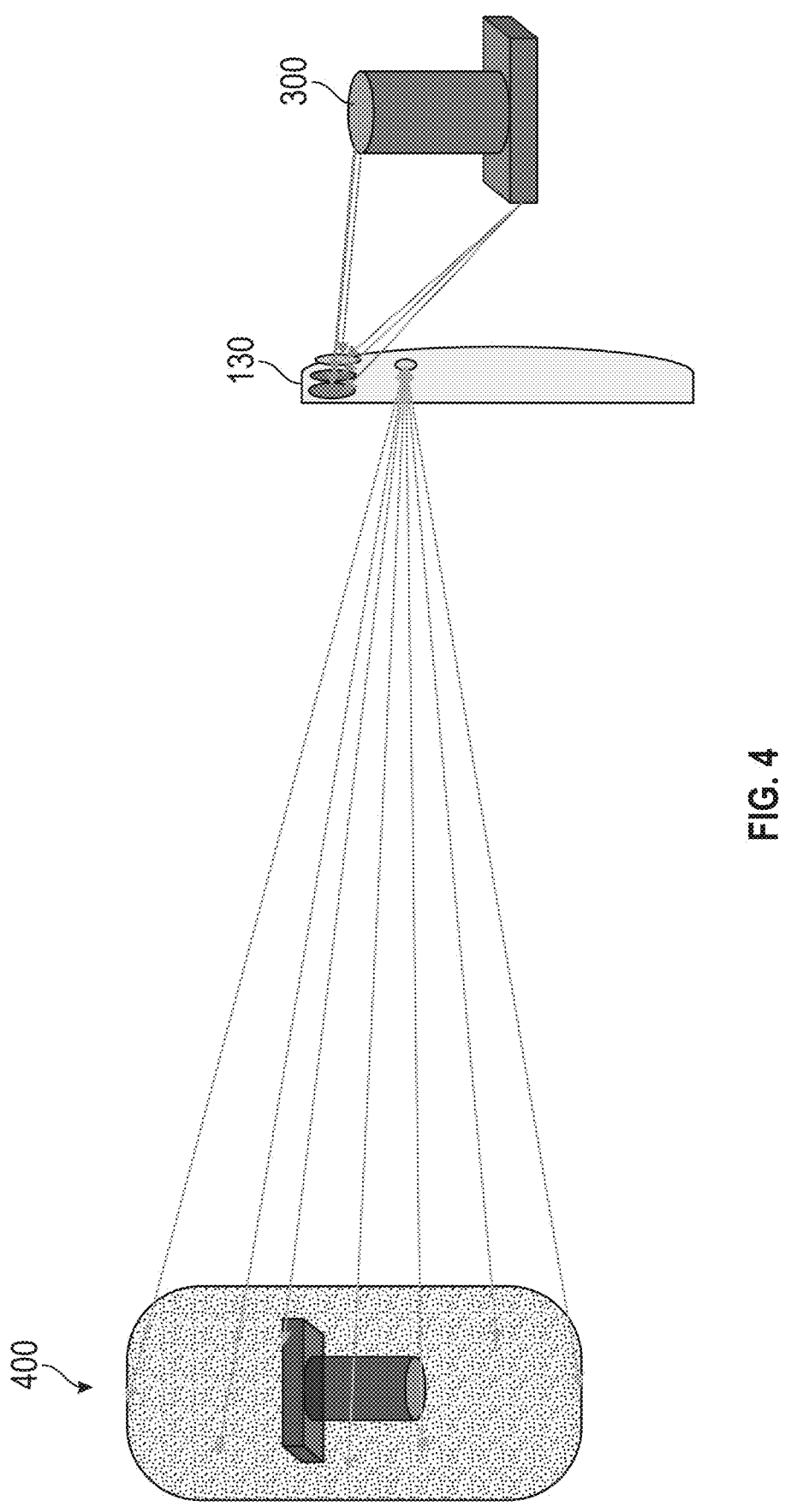
FIG. 4 illustrates an example of projecting an image onto a user's retina via a virtual retinal display of a vocational mask according to certain embodiments of this disclosure.

FIG. 4 illustrates an example of projecting an image onto a user's retina 400 via a virtual retinal display of a vocational mask 130 according to certain embodiments of this disclosure. As depicted, the imagers and/or cameras of the vocational mask 130 receive data pertaining to the object and the vocational mask 130 processes the data and projects an image representing the object 300 using a virtual retinal display onto the user's retina 400. The bidirectional communication with other users (e.g., students, master user, collaborator, teacher, supervisor, etc.) may enable projecting the image onto their retinas if they are wearing a vocational mask, as well. In some embodiments, the image may be displayed via a computing device 140 if the other users are not wearing vocational masks.

Figure 5:
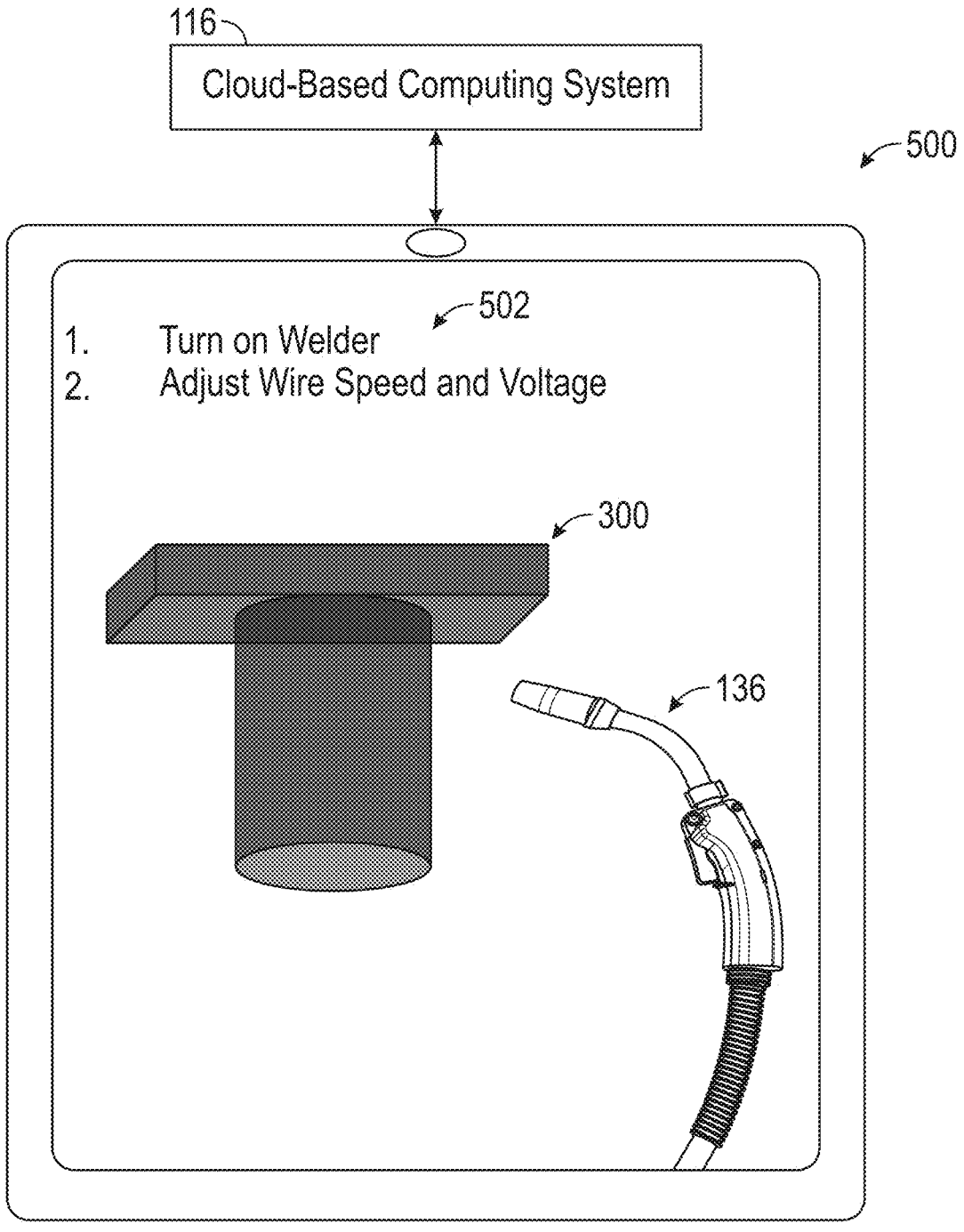
FIG. 5 illustrates an example of an image including instructions projected via a virtual retinal display of a vocational mask according to certain embodiments of this disclosure.

FIG. 5 illustrates an example of an image including instructions projected via a virtual retinal display of a vocational mask 130 according to certain embodiments of this disclosure. The example user interface 500 depicts actual things the user is looking at, such as a tool 136 and an object 300, through the vocational mask 130. Further, the user interface depicts instructions 502 pertaining to performing a task. The instructions 502 may be generated by one or more machine learning models 154 of the AI agent, or may be provided via a computing device 140 and/or other vocational mask being used by another user (e.g., master user, collaborator, teacher, supervisor, etc.). In the depicted example, the instructions 502 instruct the user to "1. Turn on welder; 2. Adjust wire speed and voltage". The instructions 502 may be projected on the user's retina via the virtual retinal display and/or presented on a display of the vocational mask 130.

Figure 6:
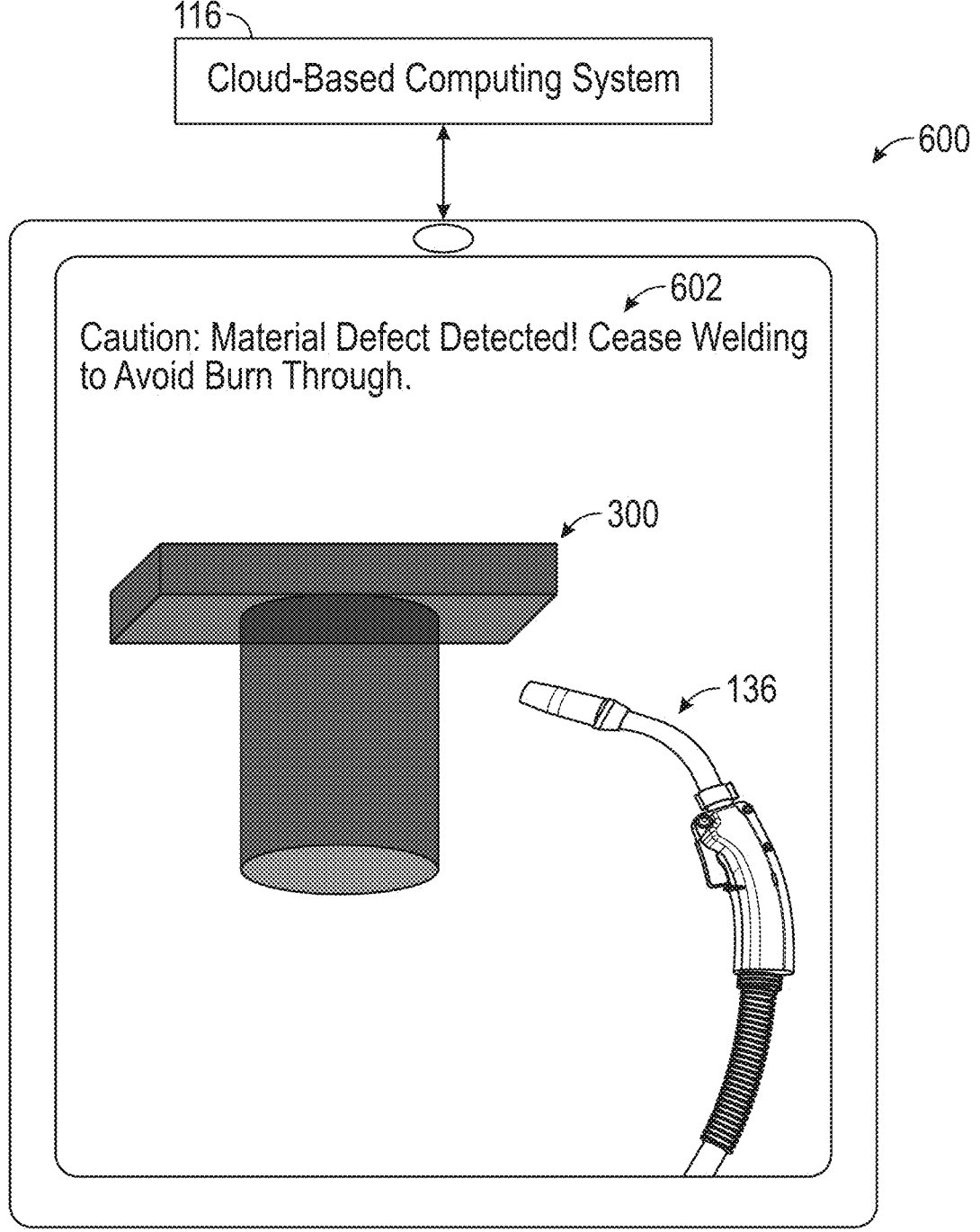
FIG. 6 illustrates an example of an image including a warning projected via a virtual retinal display of a vocational mask according to certain embodiments of this disclosure.

FIG. 6 illustrates an example of an image including a warning projected via a virtual retinal display of a vocational mask according to certain embodiments of this disclosure. The example user interface 600 depicts actual things the user is looking at, such as a tool 136 and an object 300, through the vocational mask 130. Further, the user interface depicts a warning 602 pertaining to performing a task. The warning 602 may be generated by one or more machine learning models 154 of the AI agent, or may be provided via a computing device 140 and/or other vocational mask being used by another user (e.g., master user, collaborator, teacher, supervisor, etc.). In the depicted example, the warning 602 indicates "Caution: Material defect detected! Cease welding to avoid burn through". The warning 602 may be projected on the user's retina via the virtual retinal display and/or presented on a display of the vocational mask 130.

FIG. 7 illustrates an example of a method 700 for executing an artificial intelligence agent to determine certain information projected via a vocational mask of a user according to certain embodiments of this disclosure. The method 700 may be performed by processing logic that may include hardware (circuitry, dedicated logic, etc.), software, or a combination of both. The method 700 and/or each of their individual functions, subroutines, or operations may be performed by one or more processing devices of a computing device (e.g., any component (server 128, training engine 152, machine learning models 154, etc.) of cloud-based computing system 116, vocational mask 130, edge processor 132 (132.1, 132.2), peripheral haptic device 134, tool 136, and/or computing device 140 of FIG. 1) implementing the method 700. The method 700 may be implemented as computer instructions stored on a memory device and executable by the one or more processors. In certain implementations, the method 700 may be performed by a single processing thread. Alternatively, the method 700 may be performed by two or more processing threads, each thread implementing one or more individual functions, routines, subroutines, or operations of the methods.

For simplicity of explanation, the method 700 is depicted and described as a series of operations. However, operations in accordance with this disclosure can occur in various orders or concurrently, and with other operations not presented and described herein. For example, the operations depicted in the method 700 may occur in combination with any other operation of any other method disclosed herein. Furthermore, not all illustrated operations may be required to implement the method 700 in accordance with the disclosed subject matter. In addition, those skilled in the art will understand and appreciate that the method 700 could alternatively be represented as a series of interrelated states via a state diagram or events.

In some embodiments, one or more machine learning models may be generated and trained by the artificial intelligence engine and/or the training engine to perform one or more of the operations of the methods described herein. For example, to perform the one or more operations, the processing device may execute the one or more machine learning models. In some embodiments, the one or more machine learning models may be iteratively retrained to select different features capable of enabling optimization of output. The features that may be modified may include a number of nodes included in each layer of the machine learning models, an objective function executed at each node, a number of layers, various weights associated with outputs of each node, and the like.

In some embodiments, a system may include the vocational mask 130, which may include one or more virtual retinal displays, memory devices, processing devices, and other components as described herein. The processing devices may be communicatively coupled to the memory devices that store computer instructions, and the processing devices may execute the computer instructions to perform one or more of the steps of the method 700. In some embodiments, the system may include a welding helmet and the vocational mask may be coupled to the welding helmet. In some embodiments, the vocational mask may be configured to operate across both visible light and high intensity ultraviolet light conditions. In some embodiments, the vocational mask may provide protection against welding flash. In some embodiments, the vocational mask may be integrated with goggles. In some embodiments, the vocational mask may be integrated with binoculars or a monocular.

At block 702, the processing device may execute an artificial intelligence agent trained to perform at least one or more functions to determine certain information. The functions may include (i) identifying perception-based objects and features, (ii) determining cognition-based scenery to identify one or more material defects, one or more assembly defects, one or more acceptable features, or some combination thereof, and (iii) determining one or more recommendations, instructions, or both.

The artificial intelligence agent may include one or more machine learning models 154 trained to perform the functions. For example, one or more machine learning models 154 may be trained to (i) identify perception-based objects and features using training data that includes labeled inputs of images including certain objects and features mapped to labeled outputs of identities or characterizations of those objects and features. The machine learning models may be trained to analyze aspects of the objects and features to compare the aspects to known aspects associated with known objects and features, and the machine learning models may perceive the identity of the analyzed objects and features.

The one or more machine learning models 154 may be trained to (ii) determine cognition-based scenery to identify one or more material defects, one or more assembly defects, one or more acceptable features, or some combination thereof using training data that includes labeled input of scenery images of objects including material defects, assembly defects, and/or acceptable features mapped to labeled outputs that characterize and/or identify the material defects, assembly defects, and/or acceptable features. For example, one scenery image may include a portion of a submarine that includes parts that are welded together, and the machine learning models may be trained to cognitively analyze the scenery image to identify one or more portions of the scenery image that includes a welded part with a material welding defect, a part assembly defect, and/or acceptable welded feature.

The one or more machine learning models 154 may be trained to (iii) determine one or more recommendations, instructions, or both using training data including labeled input of images (e.g., objects, products, tools, actions, etc.) and tasks to be performed (e.g., weld, grind, chamfer, debur, sand, polish, coat, etc.) mapped to labeled outputs including recommendations, instructions, or both. The processing device may provide (e.g., via the virtual retinal display, a speaker, etc.) images, video, and/or audio that points out the defects and provides instructions, drawings, and/or information pertaining to how to fix the defects.

In addition, the output from performing one of the functions (i), (ii), and/or (iii) may be used as input to the other functions to enable the machine learning models 154 to generate a combined output. For example, the machine learning models 154 may identify a defect (a gouge) and provide welding instructions on how to fix the defect by filling the gouge properly via the vocational mask 130. Further, in some instances, the machine learning models 154 may identify several potential actions that the user can perform to complete the task and may aid the user's decision making by providing the actions in a ranked order of most preferred action to least preferred action or a ranked order of the action with the highest probability of success to the action with the lowest probability of success. In some embodiments, the machine learning models 154 may identify an acceptable feature (e.g., properly welded parts) and may output a recommendation to do nothing.

At block 704, the processing device may cause the certain information to be presented via the virtual retinal display. In some embodiments, the virtual retinal display may project an image onto at least one iris of the user to display alphanumeric data, graphic instructions, animated instructions, video instructions, or some combination thereof. In some embodiments, the vocational mask may include a stereo speaker to emit audio pertaining the information. In some embodiments, the processing device may superposition the certain information on a display (e.g., virtual retinal display).

In some embodiments, the vocational mask may include a network interface configured to enable bidirectional communication with a second network interface of a second vocational mask. The bidirectional communication may enable transmission of real-time or near real-time audio and video data, recorded audio and video data, or some combination thereof. "Real-time" may refer to less than 2 seconds and "near real-time" may refer to between 2 and 20 seconds.

In some embodiments, in addition to the vocational mask, a system may include a peripheral haptic device. The vocational mask may include a haptic interface, and the haptic interface may be configured to perform bidirectional haptic sensing and stimulation using the peripheral haptic device and the bidirectional communication. The stimulation may include precise mimicking, vibration, and the like. For example, the stimulation may include performing mimicked gestures via the peripheral haptic device. In other words, a master user may be using a peripheral haptic device to perform a task and the gestures performed by the master user using the peripheral haptic device may be mimicked by the peripheral haptic device being used by an apprentice user. In such a way, the master user may train and/or guide the apprentice user how to properly perform a task (e.g., weld) using the peripheral haptic devices.

The haptic interface may be communicatively coupled to the processing device. The haptic interface may be configured to sense, from the peripheral haptic device, hand motions, texture, temperature, vibration, slipperiness, friction, wetness, pulsation, stiction, friction, and the like. For example, the haptic interface may detect keystrokes when a user uses a virtual keyboard presented via the vocational mask using a display (e.g., virtual retinal display).

Further, the bidirectional communication provided by the vocational mask(s) and/or computing devices may enable a master user of a vocational mask and/or computing device to view and/or listen to the real-time or near real-time audio and video data, recorded audio and video data, or some combination thereof, and to provide instructions to the user via the vocational mask being worn by the user. In some embodiments, the bidirectional communication provided by the vocational mask(s) and/or computing devices may enable the user of a vocational mask and/or computing device to provide instructions to a set of students and/or apprentices via multiple vocational masks being worn by the students and/or apprentices. This technique may be beneficial for a teacher, collaborator, master user, and/or supervisor that is training the set of students.

In some embodiments, the user wearing a vocational mask may communicate with one or more users who are not wearing a vocational mask. For example, a teacher and/or collaborator may be using a computing device (e.g., smartphone) to see what a student is viewing and hear what the student is hearing using the bidirectional communication provided by the vocational mask worn by the student. The bidirectional communication provided by the vocational mask may enable a teacher or collaborator to receive, using a computing device, audio data, video data, haptic data, or some combination thereof, from the vocational mask being used by the user.

Additionally, the teacher and/or collaborator may receive haptic data, via the computing device, from the vocational mask worn by the student. The teacher and/or collaborator may transmit instructions (e.g., audio, video, haptic, etc.), via the computing device, to the vocational mask to guide and/or teach the student how to perform the task (e.g., weld) in real-time or near real-time.

In another example, the bidirectional communication may enable a user wearing a vocational mask to provide instructions to a set of students via a set of computing devices (e.g., smartphones). In this example, the user may be a teacher or collaborator and may be teaching a class or lesson on how to perform a task (e.g., weld) while wearing the vocational mask.

In some embodiments, the vocational mask may include one or more sensors to provide information related to geographical position, pose of the user, rotational rate of the user, or some combination thereof. In some embodiments, a position sensor may be used to determine a location of the vocational mask, an object, a peripheral haptic device, a tool, etc. in a physical space. The position sensor may determine an absolute position in relation to an established reference point. In some embodiments, the processing device may perform physical registration of the vocational mask, an object being worked on, a peripheral haptic device, a tool (e.g., welding gun, sander, grinder, etc.), etc. to map out the device in an environment (e.g., warehouse, room, underwater, etc.) in which the vocational mask, the object, the peripheral haptic device, etc. is located.

In some embodiments, the vocational mask may include one or more sensors including vocation imaging band specific cameras, visual band cameras, stereo microphones, acoustic sensors, or some combination thereof. The acoustic sensors may sense welding clues based on audio signatures associated with certain defects or issues, such as burn through. Machine learning models 154 may be trained using inputs of labeled audio signatures, labeled images, and/or labeled videos mapped to labeled outputs of defects. The artificial intelligence agent may process received sensor data, such as images, audio, video, haptics, etc., identify an issue (e.g., defect), and provide a recommendation (e.g., stop welding due to detected potential burn through) via the vocational mask.

In some embodiments, the vocational mask may include an optical bench that aligns the virtual retinal display to one or more eyes of the user.

In some embodiments, the processing device is configured to record the certain information, communications with other devices (e.g., vocational masks, computing devices), or both. The processing device may store certain information and/or communications as data in the memory device communicatively coupled to the processing device, and/or the processing device may transmit the certain information and/or communications as data feeds to the cloud-based computing system 116 for storage.

FIG. 8 illustrates an example of a method 800 for transmitting instructions for performing a task via bidirectional communication between a vocational mask and a computing device according to certain embodiments of this disclosure. The method 800 may be performed by processing logic that may include hardware (circuitry, dedicated logic, etc.), software, or a combination of both. The method 800 and/or each of their individual functions, subroutines, or operations may be performed by one or more processing devices of a computing device (e.g., any component (server 128, training engine 152, machine learning models 154, etc.) of cloud-based computing system 116, vocational mask 130, edge processor 132 (132.1, 132.2), peripheral haptic device 134, tool 136, and/or computing device 140 of FIG. 1) implementing the method 700. The method 800 may be implemented as computer instructions stored on a memory device and executable by the one or more processors. In certain implementations, the method 800 may be performed by a single processing thread. Alternatively, the method 800 may be performed by two or more processing threads, each thread implementing one or more individual functions, routines, subroutines, or operations of the methods.

For simplicity of explanation, the method 800 is depicted and described as a series of operations. However, operations in accordance with this disclosure can occur in various orders or concurrently, and with other operations not presented and described herein. For example, the operations depicted in the method 800 may occur in combination with any other operation of any other method disclosed herein. Furthermore, not all illustrated operations may be required to implement the method 800 in accordance with the disclosed subject matter. In addition, those skilled in the art will understand and appreciate that the method 800 could alternatively be represented as a series of interrelated states via a state diagram or events.

In some embodiments, one or more machine learning models may be generated and trained by the artificial intelligence engine and/or the training engine to perform one or more of the operations of the methods described herein. For example, to perform the one or more operations, the processing device may execute the one or more machine learning models. In some embodiments, the one or more machine learning models may be iteratively retrained to select different features capable of enabling optimization of output. The features that may be modified may include a number of nodes included in each layer of the machine learning models, an objective function executed at each node, a number of layers, various weights associated with outputs of each node, and the like.

At block 802, while a first user wears a vocational mask 130 to perform a task, the processing device may receive, at one or more processing devices of the vocational mask 130, one or more first data feeds from one or more cameras of the vocational mask 130, sensors of the vocational mask 130, peripheral haptic devices associated with the vocational mask 130, microphones of the vocational mask 130, or some combination thereof. In some embodiments, the vocational mask 130 may be attached to or integrated with a welding helmet and the task may be welding. In some embodiments, the task may be sanding, grinding, polishing, deburring, chamfering, coating, etc. The vocational mask 130 may be attached to or integrated with a helmet, a hat, goggles, binoculars, a monocular, or the like.

In some embodiments, the one or more first data feeds may include information related to video, images, audio, hand motions, haptics, texture, temperature, vibration, slipperiness, friction, wetness, pulsation, or some combination thereof. In some embodiments, the one or more first data feeds may include geographical position of the vocational mask 130, and the processing device may map, based on the geographical positon, the vocational mask 130 in an environment or a physical space in which the vocational mask 130 is located.

At block 804, the processing device may transmit, via one or more network interfaces of the vocational mask 130, the one or more first data feeds to one or more processing devices of the computing device 140 of a second user. In some embodiments, the computing device 140 of the second user may include one or more vocational masks, one or more smartphones, one or more tablets, one or more laptop computers, one or more desktop computers, one or more servers, or some combination thereof. The computing device 140 may be separate from the vocational mask 130, and the one or more first data feeds are at least one of presented via a display of the computing device 140, emitted by an audio device of the computing device 140, or produced or reproduced via a peripheral haptic device coupled to the computing device 140. In some embodiments, the first user may be an apprentice, student, trainee, or the like, and the second user may be a master user, a trainer, a teacher, a collaborator, a supervisor, or the like.

At block 806, the processing device may receive, from the computing device, one or more second data feeds pertaining to at least instructions for performing the task. The one or more second data feeds are received by the one or more processing devices of the vocational mask 130, and the one or more second data feeds are at least one of presented via a virtual retinal display of the vocational mask 130, emitted by an audio device (e.g., speaker) of the vocational mask 130, or produced or reproduced via a peripheral haptic device 134 coupled to the vocational mask 130.

In some embodiments, the instructions are presented, by the virtual retinal display of the vocational mask 130, via augmented reality. In some embodiments, the instructions are presented, by the virtual retinal display of the vocational mask, via virtual reality during a simulation associated with the task. In some embodiments, the processing device may cause the virtual retinal display to project an image onto at least one iris of the first user to display alphanumeric data associated with the instructions, graphics associated with the instructions, animations associated with the instructions, video associated with the instructions, or some combination thereof.

At block 808, the processing device may store, via one or more memory devices communicatively coupled to the one or more processing devices of the vocational mask 130, the one or more first data feeds and/or the one or more second data feeds.

In some embodiments, the processing device may cause the peripheral haptic device 130 to vibrate based on the instructions received from the computing device 140.

In some embodiments, the processing device may execute an artificial intelligence agent trained to perform at least one or more functions to determine certain information. The one or more functions may include (i) identifying perception-based objects and features, (ii) determining cognition-based scenery to identify one or more material defects, one or more assembly defects, one or more acceptable features, or some combination thereof, and (iii) determining one or more recommendations, instructions, or both.

FIG. 9 illustrates an example of a method 900 for implementing instructions for performing a task using a peripheral haptic device according to certain embodiments of this disclosure. The method 900 may be performed by processing logic that may include hardware (circuitry, dedicated logic, etc.), software, or a combination of both. The method 900 and/or each of their individual functions, subroutines, or operations may be performed by one or more processing devices of a computing device (e.g., any component (server 128, training engine 152, machine learning models 154, etc.) of cloud-based computing system 116, vocational mask 130, edge processor 132 (132.1, 132.2), peripheral haptic device 134, tool 136, and/or computing device 140 of FIG. 1) implementing the method 900. The method 900 may be implemented as computer instructions stored on a memory device and executable by the one or more processors. In certain implementations, the method 900 may be performed by a single processing thread. Alternatively, the method 900 may be performed by two or more processing threads, each thread implementing one or more individual functions, routines, subroutines, or operations of the methods.

For simplicity of explanation, the method 900 is depicted and described as a series of operations. However, operations in accordance with this disclosure can occur in various orders or concurrently, and with other operations not presented and described herein. For example, the operations depicted in the method 900 may occur in combination with any other operation of any other method disclosed herein. Furthermore, not all illustrated operations may be required to implement the method 900 in accordance with the disclosed subject matter. In addition, those skilled in the art will understand and appreciate that the method 900 could alternatively be represented as a series of interrelated states via a state diagram or events.

In some embodiments, one or more machine learning models may be generated and trained by the artificial intelligence engine and/or the training engine to perform one or more of the operations of the methods described herein. For example, to perform the one or more operations, the processing device may execute the one or more machine learning models. In some embodiments, the one or more machine learning models may be iteratively retrained to select different features capable of enabling optimization of output. The features that may be modified may include a number of nodes included in each layer of the machine learning models, an objective function executed at each node, a number of layers, various weights associated with outputs of each node, and the like.

At block 902, the processing device may receive, at one or more processing devices of a vocational mask 130, first data pertaining to instructions for performing a task using a tool 136. The first data may be received from a computing device 140 separate from the vocational mask 130. In some embodiments, the computing device may include one or more peripheral haptic devices, one or more vocational masks, one or more smartphones, one or more tablets, one or more laptop computers, one or more desktop computers, one or more servers, or some combination thereof. In some embodiments, the task includes welding and the tool 136 is a welding gun.

At block 904, the processing device may transmit, via a haptic interface communicatively coupled to the one or more processing devices of the vocational mask 130, the first data to one or more peripheral haptic devices 134 associated with the tool 136 to cause the one or more peripheral haptic devices 134 to implement the instructions by at least vibrating in accordance with the instructions to guide a user to perform the task using the tool 136.

At block 906, responsive to the one or more peripheral haptic devices 134 implementing the instructions, the processing device may receive, from a haptic interface, feedback data pertaining to one or more gestures, motions, surfaces, temperatures, or some combination thereof. The feedback data may be received from the one or more peripheral haptic devices 134, and the feedback data may include information pertaining to the user's compliance with the instructions for performing the task.

At block 908, the processing device may transmit, to the computing device 140, the feedback data. In some embodiments, transmitting the feedback data may cause the computing device 140 to produce an indication of whether the user complied with the instructions for performing the task. The indication may be produced or generated via a display, a speaker, a different peripheral haptic device, or some combination thereof.

In some embodiments, in addition to the first data being received, video data may be received at the processing device of the vocational mask 130, and the video data may include video pertaining to the instructions for performing the task using the tool 136. In some embodiments, the processing device may display, via a virtual retinal display of the vocational mask 130, the video data. In some embodiments, the video data may be displayed concurrently with the instructions being implemented by the one or more peripheral haptic devices 134.

In some embodiments, in addition to the first data and/or video data being received, audio data may be received at the processing device of the vocational mask 130, and the audio data may include audio pertaining to the instructions for performing the task using the tool 136. In some embodiments, the processing device may emit, via a speaker of the vocational mask 130, the audio data. In some embodiments, the audio data may be emitted concurrently with the instructions being by the one or more peripheral haptic devices 134 and/or with the video data being displayed by the virtual retinal display. That is, one or more of video, audio, and/or haptic data pertaining to the instructions may be used concurrently to guide or instruct a user how to perform a task.

In some embodiments, in addition to the first data, video data, and/or audio data being received, virtual reality data may be received at the processing device of the vocational mask 130, and the virtual reality data may include virtual reality multimedia representing a simulation of a task. The processing device may execute, via at least a display of the vocational mask 130, playback of the virtual reality multimedia. For example, an artificial intelligent simulation generator may be configured to generate a virtual reality simulation for performing a task, such as welding an object using a welding gun. The virtual reality simulation may take into consideration various attributes, characteristics, parameters, and the like of the welding scenario, such as type of object being welded, type of welding, current amperage, length of arc, angle, manipulation, speed, and the like. The virtual reality simulation may be generated as multimedia that is presented via the vocational mask to a user to enable a user to practice, visualize, and experience performing certain welding tasks without actually welding anything.

In some embodiments, in addition to the first data, video data, audio data, and/or virtual reality data being received, augmented reality data may be received at the processing device of the vocational mask 130, and the augmented reality data may include augmented reality multimedia representing at least the instructions (e.g., via text, graphics, images, video, animation, audio). The processing device may execute, via at least a display of the vocational mask 130, playback of the augmented reality multimedia.

In some embodiments, the processing device may execute an artificial intelligence agent trained to perform at least one or more functions to determine certain information. The one or more functions may include (i) identifying perception-based objects and features, (ii) determining cognition-based scenery to identify one or more material defects, one or more assembly defects, one or more acceptable features, or some combination thereof, and/or (iii) determining one or more recommendations, instructions, or both. In some embodiments, the processing device may display, via a display (e.g., virtual retinal display or other display), the objects and features, the one or more material defects, the one or more assembly defects, the one or more acceptable features, the one or more recommendations, the instructions, or some combination thereof.

Figure 10:
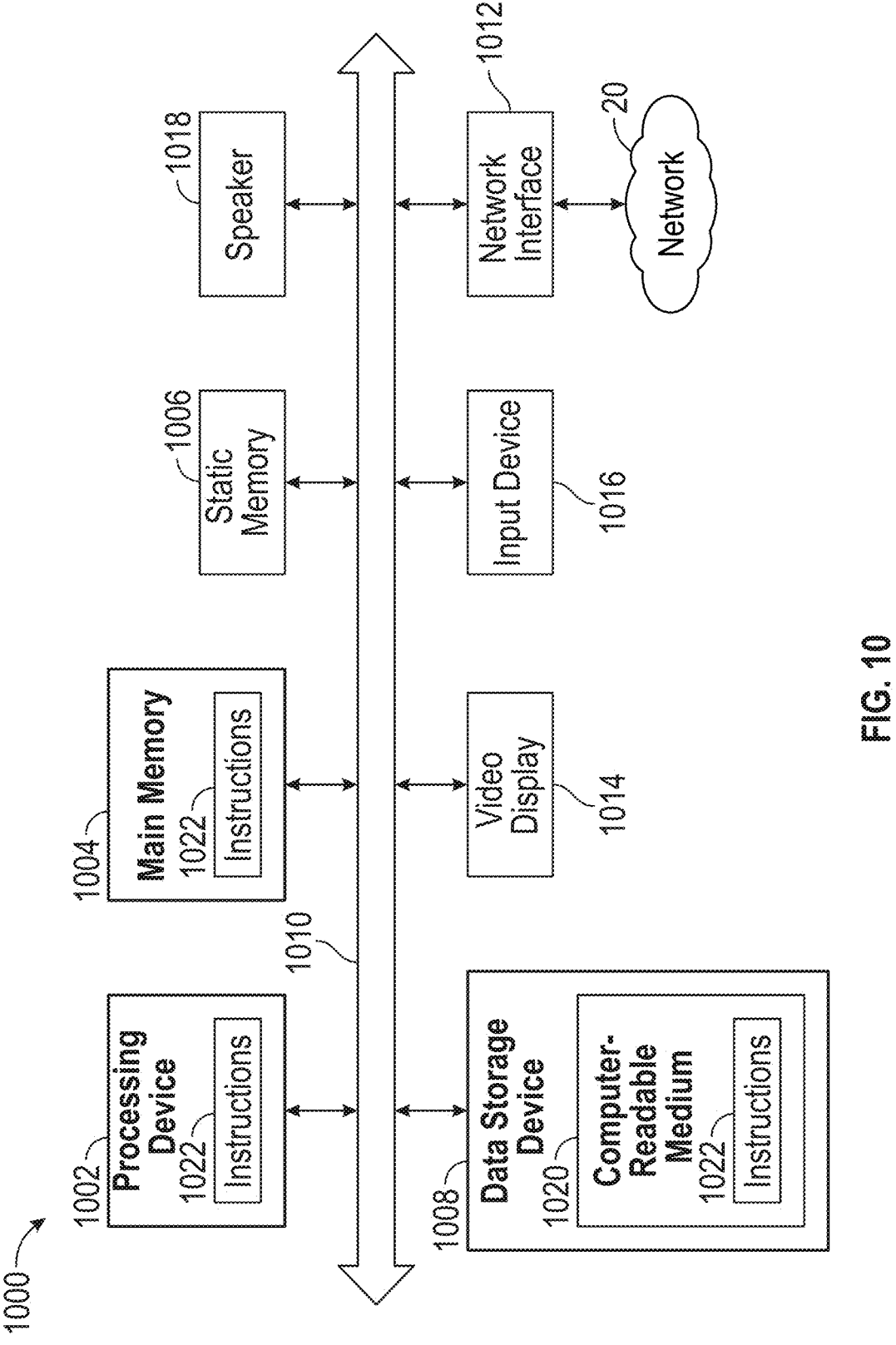
FIG. 10 illustrates an example computer system according to embodiments of this disclosure.

FIG. 10 illustrates an example computer system 1000, which can perform any one or more of the methods described herein. In one example, computer system 1000 may include one or more components that correspond to the vocational mask 130, the computing device 140, the peripheral haptic device 134, the tool 136, one or more servers 128 of the cloud-based computing system 116, or one or more training engines 152 of the cloud-based computing system 116 of FIG. 1. The computer system 1000 may be connected (e.g., networked) to other computer systems in a LAN, an intranet, an extranet, or the Internet. The computer system 1000 may operate in the capacity of a server in a client-server network environment. The computer system 1000 may be a personal computer (PC), a tablet computer, a laptop, a wearable (e.g., wristband), a set-top box (STB), a personal Digital Assistant (PDA), a smartphone, a smartwatch, a camera, a video camera, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1000 includes a processing device 1002, a main memory 1004 (e.g., read-only memory (ROM), solid state drive (SSD), flash memory, dynamic random access memory (DRAM) such as synchronous DRAM (SDRAM)), a static memory 1006 (e.g., solid state drive (SSD), flash memory, static random access memory (SRAM)), and a data storage device 1008, which communicate with each other via a bus 1010.

Processing device 1002 represents one or more general-purpose processing devices such as a microprocessor, central processing unit, or the like. More particularly, the processing device 1002 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1002 may also be one or more special-purpose processing devices such as an application specific integrated circuit (ASIC), a field programmable gate array (FPGA), a digital signal processor (DSP), network processor, or the like. The processing device 1002 is configured to execute instructions for performing any of the operations and steps of any of the methods discussed herein.

The computer system 1000 may further include a network interface device 1012. The computer system 1000 also may include a video display 1014 (e.g., a liquid crystal display (LCD) or a cathode ray tube (CRT)), one or more input devices 1016 (e.g., a keyboard and/or a mouse), and one or more speakers 1018 (e.g., a speaker). In one illustrative example, the video display 1014 and the input device(s) 1016 may be combined into a single component or device (e.g., an LCD touch screen).

The data storage device 1016 may include a computer-readable medium 1020 on which the instructions 1022 embodying any one or more of the methodologies or functions described herein are stored. The instructions 1022 may also reside, completely or at least partially, within the main memory 1004 and/or within the processing device 1002 during execution thereof by the computer system 1000. As such, the main memory 1004 and the processing device 1002 also constitute computer-readable media. The instructions 1022 may further be transmitted or received over a network 20 via the network interface device 1012.

While the computer-readable storage medium 1020 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

The foregoing description, for purposes of explanation, used specific nomenclature to provide a thorough understanding of the described embodiments. However, it should be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

CLAUSES

Clause 1. A system comprising:
a vocational mask configured to be worn by a user, wherein the vocational mask comprises:
a virtual retinal display;
a memory device storing instructions;
a processing device communicatively coupled to the memory device and the virtual retinal display, wherein the processing device executes the instructions to:
execute an artificial intelligence agent trained to perform at least one or more functions to determine certain information, wherein the one or more functions comprise:
identifying perception-based objects and features,
determining cognition-based scenery to identify one or more material defects, one or more assembly defects, one or more acceptable features, or some combination thereof, and
determining one or more recommendations, instructions, or both; and
cause the certain information to be presented via the virtual retinal display.

Clause 2. The system of any clause herein, wherein the virtual retinal display projects an image onto at least one iris of the user to display alphanumeric data, graphic instructions, animated instructions, video instructions, or some combination thereof.

Clause 3. The system of any clause herein, wherein the vocational mask further comprises a network interface configured to enable bidirectional communication with a second network interface of a second vocational mask, and the bidirectional communication enables transmission of real-time or near real-time audio and video data, recorded audio and video data, or some combination thereof.

Clause 4. The system of any clause herein, further comprising a peripheral haptic device, wherein:
the vocational mask further comprises a haptic interface, and wherein the haptic interface is configured to perform bidirectional haptic sensing and stimulation using the peripheral haptic device and the bidirectional communication, and wherein the stimulation comprises performing mimicked gestures via the peripheral haptic device.

Clause 5. The system of any clause herein, wherein the bidirectional communication enables a master user of the second vocational mask to view and/or listen to the real-time or near real-time audio and video data, recorded audio and video data, or some combination thereof, and to provide instructions to the user via the vocational mask.

Clause 6. The system of any clause herein, wherein bidirectional communication enables the user of the vocational mask to provide instructions to a plurality of students via a plurality of vocational masks.

Clause 7. The system of any clause herein, wherein bidirectional communication enables the user of the vocational mask to provide instructions to a plurality of students via a plurality of computing devices.

Clause 8. The system of any clause herein, wherein bidirectional communication enables a collaborator or teacher to receive, using a computing device, audio data, video data, haptic data, or some combination thereof, from the vocational mask being used by the user.

Clause 9. The system of any clause herein, further comprising a cloud-based computing system communicatively coupled to the vocational mask, wherein:

the cloud-based computing system determines one or more parameters by training a cloud-based artificial intelligence agent using training data to perform the one or more functions, and the cloud-based computing system transmits the one or more parameters to the vocational mask to train the artificial intelligence agent.

Clause 10. The system of any clause herein, wherein the vocational mask further comprises a haptic interface communicatively coupled to the processing device, wherein the haptic interface is configured to sense hand motions, texture, temperature, vibration, slipperiness, friction, wetness, pulsation, or some combination thereof.

Clause 11. The system of any clause herein, wherein the system further comprises a welding helmet and the vocational mask is coupled to the welding helmet.

Clause 12. The system of any clause herein, wherein the vocational mask further comprises a stereo speaker to emit audio pertaining to the certain information.

Clause 13. The system of any clause herein, wherein the vocational mask further comprises one or more sensors to provide information related to geographical position, pose of the user, rotational rate of pose of the user, or some combination thereof.

Clause 14. The system of any clause herein, wherein the vocational mask further comprises one or more sensors comprising vocation imaging band specific cameras, visual band cameras, stereo microphones, acoustic sensors, or some combination thereof.

Clause 15. The system of any clause herein, wherein the vocational mask further comprises an optical bench that aligns the virtual retinal display to one or more eyes of the user.

Clause 16. The system of any clause herein, wherein the processing device executes the instructions to superposition the certain information on a display.

Clause 17. The system of any clause herein, wherein the vocational mask is configured to operate across both visible light and high intensity ultraviolet light conditions.

Clause 18. The system of any clause herein, wherein the processing device is configured to record the certain information, communications with other devices, or both.

Clause 19. The system of any clause herein, wherein the vocational mask provides protection against welding flash.

Clause 20. The system of any clause herein, wherein the processing device executes the instructions to map the vocational mask in a physical space in which the vocational mask is located.

Clause 21. The system of any clause herein, wherein the vocational mask comprises goggles.

Clause 22. A vocational mask configured to be worn by a user, wherein the vocational mask comprises:

a virtual retinal display;

a memory device storing instructions;

a processing device communicatively coupled to the memory device and the virtual retinal display, wherein the processing device executes the instructions to:

execute an artificial intelligence agent trained to perform at least one or more functions to determine certain information, wherein the one or more functions comprise: identifying perception-based objects and features, determining cognition-based scenery to identify one or more material defects, one or more assembly defects, one or more acceptable features, or some combination thereof, and determining one or more recommendations, instructions, or both; and cause the certain information to be presented via the virtual retinal display.

Clause 23. A computer-implemented method comprising:

executing, by one or more processing devices of a vocational mask, an artificial intelligence agent trained to perform at least one or more functions to determine certain information, wherein the one or more functions comprise:

identifying perception-based objects and features, determining cognition-based scenery to identify one or more material defects, one or more assembly defects, one or more acceptable features, or some combination thereof, and determining one or more recommendations, instructions, or both; and causing, by the one or more processing devices, the certain information to be presented via a virtual retinal display of the vocational mask.

Clause 24. The system of claim 1, wherein the processing device stores communications in the memory device, wherein the communications are between the vocational mask and another vocational mask, the vocational mask and a computing device, or both.

Clause 25. A system comprising:

goggles configured to be worn by a user, wherein the goggles comprise:

a display;

a memory device storing instructions;

a processing device communicatively coupled to the memory device and the display, wherein the processing device executes the instructions to:

execute an artificial intelligence agent trained to perform at least one or more functions to determine certain information, wherein the one or more functions comprise:

identifying perception-based objects and features, determining cognition-based scenery to identify one or more material defects, one or more assembly defects, one or more acceptable features, or some combination thereof, and determining one or more recommendations, instructions, or both; and cause the certain information to be presented via the display.

Clause 26. A system comprising:

a monocular welding goggle configured to be worn by a user, wherein the monocular welding goggle comprises:

a display;

a memory device storing instructions;

a processing device communicatively coupled to the memory device and the display, wherein the processing device executes the instructions to:

execute an artificial intelligence agent trained to perform at least one or more functions to determine certain information, wherein the one or more functions comprise:

identifying perception-based objects and features, determining cognition-based scenery to identify one or more material defects, one or more assembly defects, one or more acceptable features, or some combination thereof, and determining one or more recommendations, instructions, or both; and cause the certain information to be presented via the display.

Clause 27. A computer-implemented method comprising:

while a first user wears a vocational mask to perform a task, receiving, at one or more processing devices of the vocational mask, one or more first data feeds from one or more cameras, sensors, peripheral haptic devices, microphones, or some combination thereof;

transmitting, via one or more network interfaces of the vocational mask, the one or more first data feeds to one or more processing devices of a computing device of a second user, wherein the computing device is separate from the vocational mask, and the one or more first data feeds are at least one of presented via a display of the computing device, emitted by an audio device of the computing device, or produced via a haptic device coupled to the computing device;

receiving, from the computing device, one or more second data feeds pertaining to at least instructions for performing the task, wherein the one or more second data feeds are received by the one or more processing devices of the vocational mask, and the one or more second data feeds are at least one of presented via a virtual retinal display of the vocational mask, emitted by an audio device of the vocational mask, or produced via a peripheral haptic device coupled to the vocational mask; and storing, via one or more memory devices communicatively coupled to the one or more processing devices of the vocational mask, the one or more first data feeds and/or the one or more second data feeds.

Clause 28. The computer-implemented method of any clause herein, wherein the computing device comprises one or more other vocational masks, one or more smartphones, one or more tablets, one or more laptop computers, one or more desktop computers, one or more servers, or some combination thereof.

Clause 29. The computer-implemented method of any clause herein, further comprising executing an artificial intelligence agent trained to perform at least one or more functions to determine certain information, wherein the one or more functions comprise:

identify perception-based objects and features, determine cognition-based scenery to identify one or more material defects, one or more assembly defects, one or more acceptable features, or some combination thereof, and determine one or more recommendations, instructions, or both.

Clause 30. The computer-implemented method of any clause herein, wherein the instructions are presented, by the virtual retinal display of the vocational mask, via augmented reality.

Clause 31. The computer-implemented method of any clause herein, wherein the instructions are presented, by the virtual retinal display of the vocational mask, via virtual reality during a simulation associated with the task.

Clause 32. The computer-implemented method of any clause herein, further comprising causing the peripheral haptic device to vibrate based on the instructions received from the computing device.

Clause 33. The computer-implemented method of any clause herein, further comprising causing the virtual retinal display to project an image onto at least one iris of the first user to display alphanumeric data associated with the instructions, graphics associated with the instructions, animations associated with the instructions, video associated with the instructions, or some combination thereof.

Clause 34. The computer-implemented method of any clause herein, wherein the first user is an apprentice and the second user is a master.

Clause 35. The computer-implemented method of any clause herein, wherein the vocational mask is attached to a welding helmet and the task is welding.

Clause 36. The computer-implemented method of any clause herein, wherein the one or more first data feeds comprise information related to video, images, audio, haptics, hand motions, texture, temperature, vibration, slipperiness, friction, wetness, pulsation, or some combination thereof.

Clause 37. The computer-implemented method of any clause herein, wherein the one or more first data feeds comprise geographical position of the vocational mask, and the method further comprises:

mapping, based on the geographical position, the vocational mask in a physical space in which the vocational mask is located.

Clause 38. The computer-implemented method of any clause herein, wherein the vocational mask comprises goggles.

Clause 39. A tangible, non-transitory computer-readable medium storing computer instructions that, when executed, cause one or more processing devices of a vocational mask to:

while a first user wears the vocational mask to perform a task, receive, at the one or more processing devices of the vocational mask, one or more first data feeds from one or more cameras, sensors, peripheral haptic devices, microphones, or some combination thereof;

transmit, via one or more network interfaces of the vocational mask, the one or more first data feeds to one or more processing devices of a computing device of a second user, wherein the computing device is separate from the vocational mask, and the one or more first data feeds are at least one of presented via a display of the computing device, emitted by an audio device of the computing device, or produced via a peripheral haptic device coupled to the computing device;

receive, from the computing device, one or more second data feeds pertaining to at least instructions for performing the task, wherein the one or more second data feeds are received by the one or more processing devices of the vocational mask, and the one or more second data feeds are at least one of presented via a virtual retinal display of the vocational mask, emitted by an audio device of the vocational mask, or produced via a peripheral haptic device coupled to the vocational mask; and store, via one or more memory devices communicatively coupled to the one or more processing devices of the vocational mask, the one or more first data feeds and/or the one or more second data feeds.

Clause 40. The computer-readable medium of any clause herein, wherein the computing device comprises one or more other vocational masks, one or more smartphones, one or more tablets, one or more laptop computers, one or more desktop computers, one or more servers, or some combination thereof.

Clause 41. The computer-readable medium of any clause herein, wherein the one or more processing devices are further to execute an artificial intelligence agent trained to perform at least one or more functions to determine certain information, wherein the one or more functions comprise:

identify perception-based objects and features, determine cognition-based scenery to identify one or more material defects, one or more assembly defects, one or more acceptable features, or some combination thereof, and determine one or more recommendations, instructions, or both.

Clause 42. The computer-readable medium of any clause herein, wherein the instructions are presented, by the virtual retinal display of the vocational mask, via augmented reality.

Clause 43. The computer-readable medium of any clause herein, wherein the instructions are presented, by the virtual retinal display of the vocational mask, via virtual reality during a simulation associated with the task.

Clause 44. The computer-readable medium of any clause herein, wherein the one or more processing devices are further to cause the peripheral haptic device to vibrate based on the instructions received from the computing device.

Clause 45. The computer-readable medium of any clause herein, wherein the one or more processing devices are further to cause the virtual retinal display to project an image onto at least one iris of the first user to display alphanumeric data associated with the instructions, graphics associated with the instructions, animations associated with the instructions, video associated with the instructions, or some combination thereof.

Clause 46. A system comprising:

a vocational mask configured to be worn by a user, wherein the vocational mask comprises:

one or more memory devices storing instructions; and one or more processing devices communicatively coupled to the one or more memory devices, wherein the one or more processing devices execute instructions to:

while a first user wears the vocational mask to perform a task, receive, at the one or more processing devices of the vocational mask, one or more first data feeds from one or more cameras, sensors, peripheral haptic devices, microphones, or some combination thereof;

transmit, via one or more network interfaces of the vocational mask, the one or more first data feeds to one or more processing devices of a computing device of a second user, wherein the computing device is separate from the vocational mask, and the one or more first data feeds are at least one of presented via a display of the computing device, emitted by an audio device of the computing device, or produced via a haptic device coupled to the computing device;

receive, from the computing device, one or more second data feeds pertaining to at least instructions for performing the task, wherein the one or more second data feeds are received by the one or more processing devices of the vocational mask, and the one or more second data feeds are at least one of presented via a virtual retinal display of the vocational mask, emitted by an audio device of the vocational mask, or produced via a peripheral haptic device coupled to the vocational mask, and; and store, via one or more memory devices communicatively coupled to the one or more processing devices of the vocational mask, the one or more first data feeds and/or the one or more second data feeds.

Clause 47. A computer-implemented method comprising:

receiving, at one or more processing devices of a vocational mask, first data pertaining to instructions for performing a task using a tool, wherein the first data is received from a computing device separate from the vocational mask;

transmitting, via a haptic interface communicatively coupled to the one or more processing devices of the vocational mask, the first data to one or more peripheral haptic devices associated with the tool to cause the one or more peripheral haptic devices to implement the instructions by at least vibrating in accordance with the instructions to guide a user to perform the task using the tool;

responsive to the one or more peripheral haptic devices implementing the instructions, receiving feedback data pertaining to one or more gestures, motions, surfaces, temperatures, or some combination thereof, wherein the feedback data is received from the one or more peripheral haptic devices, and the feedback data comprises information pertaining to the user's compliance with the instructions for performing the task; and transmitting, to the computing device, the feedback data.

Clause 48. The computer-implemented method of any clause herein, wherein transmitting the feedback data causes the computing device to produce an indication of whether the user complied with the instructions for performing the task, wherein the indication is produced via a display, a speaker, a different peripheral haptic device, or some combination thereof.

Clause 49. The computer-implemented method of any clause herein, further comprising:

receiving, at the one or more processing devices of the vocational mask, second data comprising video pertaining to the instructions for performing the task using the tool; and displaying, via a virtual retinal display of the vocational mask, the second data.

Clause 50. The computer-implemented method of any clause herein, further comprising:

receiving, at the one or more processing devices of the vocational mask, second data comprising audio pertaining the instructions for performing the task using the tool; and emitting, via a speaker of the vocational mask, the second data.

Clause 51. The computer-implemented method of any clause herein, further comprising:

receiving, at the one or more processing devices of the vocational mask, second data comprising virtual reality multimedia representing a simulation of the task; and executing, via at least a display of the vocational mask, playback of the virtual reality multimedia.

Clause 52. The computer-implemented method of any clause herein, further comprising:

receiving, at the one or more processing devices of the vocational mask, second data comprising augmented reality multimedia representing at least the instructions; and executing, via at least a display of the vocational mask, playback of the augmented reality multimedia.

Clause 53. The computer-implemented method of any clause herein, wherein the computing device comprises one or more other peripheral haptic devices, one or more other vocational masks, one or more smartphones, one or more tablets, one or more laptop computers, one or more desktop computers, one or more servers, or some combination thereof.

Clause 54. The computer-implemented method of any clause herein, wherein the task comprises welding and the tool comprises a welding gun.

Clause 55. The computer-implemented method of any clause herein, further comprising executing an artificial intelligence agent trained to perform at least one or more functions to determine certain information, wherein the one or more functions comprise:

identify perception-based objects and features, determine cognition-based scenery to identify one or more material defects, one or more assembly defects, one or more acceptable features, or some combination thereof, and determine one or more recommendations, instructions, or both.

Clause 56. The computer-implemented method of any clause herein, further comprising displaying, via a display, the objects and features, the one or more material defects, the one or more assembly defects, the one or more acceptable features, the one or more recommendations, the instructions, or some combination thereof.

Clause 57. A tangible, non-transitory computer-readable medium storing instructions that, when executed, cause one or more processing devices of a vocational mask to:

receive, at the one or more processing devices of the vocational mask, first data pertaining to instructions for performing a task using a tool, wherein the first data is received from a computing device separate from the vocational mask;

transmit, via a haptic interface communicatively coupled to the one or more processing devices of the vocational mask, the first data to one or more peripheral haptic devices associated with the tool to cause the one or more peripheral haptic devices to implement the instructions by at least vibrating in accordance with the instructions to guide a user to perform the task using the tool;

responsive to the one or more peripheral haptic devices implementing the instructions, receive feedback data pertaining to one or more gestures, motions, surfaces, temperatures, or some combination thereof, wherein the feedback data is received from the one or more peripheral haptic devices, and the feedback data comprises information pertaining to the user's compliance with the instructions for performing the task; and transmit, to the computing device, the feedback data.

Clause 58. The computer-readable medium of any clause herein, wherein transmitting the feedback data causes the computing device to produce an indication of whether the user complied with the instructions for performing the task, wherein the indication is produced via a display, a speaker, a different peripheral haptic device, or some combination thereof.

Clause 59. The computer-readable medium of any clause herein, wherein the one or more processing devices are further to:

receive, at the one or more processing devices of the vocational mask, second data comprising video pertaining to the instructions for performing the task using the tool; and display, via a virtual retinal display of the vocational mask, the second data.

Clause 60. The computer-readable medium of any clause herein, wherein the one or more processing devices are further to:

receive, at the one or more processing devices of the vocational mask, second data comprising audio pertaining the instructions for performing the task using the tool; and emit, via a speaker of the vocational mask, the second data.

Clause 61. The computer-readable medium of any clause herein, wherein the one or more processing devices are further to:

receive, at the one or more processing devices of the vocational mask, second data comprising virtual reality multimedia representing a simulation of the task; and execute, via at least a display of the vocational mask, playback of the virtual reality multimedia.

Clause 62. The computer-readable medium of any clause herein, wherein the one or more processing devices are further to:

receive, at the one or more processing devices of the vocational mask, second data comprising augmented reality multimedia representing at least the instructions; and execute, via at least a display of the vocational mask, playback of the augmented reality multimedia.

Clause 63. The computer-readable medium of any clause herein, wherein the computing device comprises one or more other peripheral haptic devices, one or more other vocational masks, one or more smartphones, one or more tablets, one or more laptop computers, one or more desktop computers, one or more servers, or some combination thereof.

Clause 64. The computer-readable medium of any clause herein, wherein the task comprises welding and the tool comprises a welding gun.

Clause 65. The computer-readable medium of any clause herein, wherein the one or more processing devices are further to execute an artificial intelligence agent trained to perform at least one or more functions to determine certain information, wherein the one or more functions comprise:

identifying perception-based objects and features, determining cognition-based scenery to identify one or more material defects, one or more assembly defects, one or more acceptable features, or some combination thereof, and determining one or more recommendations, instructions, or both.

Clause 66. A system comprising:

a vocational mask configured to be worn by a user, wherein the vocational mask comprises:

one or more memory devices storing instructions;

one or more processing devices communicatively coupled to the one or more memory devices, wherein the one or more processing devices execute the instructions to:

receive, at the one or more processing devices of the vocational mask, first data pertaining to instructions for performing a task using a tool, wherein the first data is received from a computing device separate from the vocational mask;

transmit, via a haptic interface communicatively coupled to the one or more processing devices of the vocational mask, the first data to one or more peripheral haptic devices associated with the tool to cause the one or more peripheral haptic devices to implement the instructions by at least vibrating in accordance with the instructions to guide a user to perform the task using the tool;

responsive to the one or more peripheral haptic devices implementing the instructions, receive feedback data pertaining to one or more gestures, motions, surfaces, temperatures, or some combination thereof, wherein the feedback data is received from the one or more peripheral haptic devices, and the feedback data comprises information pertaining to the user's compliance with the instructions for performing the task; and transmit, to the computing device, the feedback data.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The invention claimed is:

1. A system comprising:

a mask configured to be worn by a user, wherein the mask comprises:

a virtual retinal display;

a memory device storing instructions;

a processing device communicatively coupled to the memory device and the virtual retinal display, wherein the processing device executes the instructions to:

execute an artificial intelligence agent trained to perform at least one or more functions to determine certain information, wherein the one or more functions comprise:

identifying perception-based objects and features, determining cognition-based scenery to identify one or more material defects, one or more assembly defects, one or more acceptable features, or some combination thereof, and determining one or more recommendations, instructions, or both; and cause the certain information to be presented via the virtual retinal display on one or more retina of the user.

2. The system of claim 1, wherein the virtual retinal display projects an image onto at least one iris of the user to display alphanumeric data, graphic instructions, animated instructions, video instructions, or some combination thereof.

3. The system of claim 1, wherein the mask further comprises a network interface configured to enable bidirectional communication with a second network interface of a second mask, and the bidirectional communication enables transmission of real-time or near real-time audio and video data, recorded audio and video data, or some combination thereof.

4. The system of claim 3, further comprising a peripheral haptic device, wherein:

the mask further comprises a haptic interface, and wherein the haptic interface is configured to perform bidirectional haptic sensing and stimulation using the peripheral haptic device and the bidirectional communication, and wherein the stimulation comprises performing mimicked gestures via the peripheral haptic device.

5. The system of claim 3, wherein the bidirectional communication enables a master user of the second mask to view and/or listen to the real-time or near real-time audio and video data, recorded audio and video data, or some combination thereof, and to provide instructions to the user via the mask.

6. The system of claim 1, wherein bidirectional communication enables the user of the mask to provide instructions to a plurality of students via a plurality of masks.

7. The system of claim 1, wherein bidirectional communication enables the user of the mask to provide instructions to a plurality of students via a plurality of computing devices.

8. The system of claim 1, wherein bidirectional communication enables a collaborator or teacher to receive, using a computing device, audio data, video data, haptic data, or some combination thereof, from the mask being used by the user.

9. The system of claim 1, further comprising a cloud-based computing system communicatively coupled to the mask, wherein:

the cloud-based computing system determines one or more parameters by training a cloud-based artificial intelligence agent using training data to perform the one or more functions, and the cloud-based computing system transmits the one or more parameters to the mask to train the artificial intelligence agent.

10. The system of claim 1, wherein the mask further comprises a haptic interface communicatively coupled to the processing device, wherein the haptic interface is configured to sense hand motions, texture, temperature, vibration, slipperiness, friction, wetness, pulsation, or some combination thereof.

11. The system of claim 1, wherein the system further comprises a welding helmet and the mask is coupled to the welding helmet.

12. The system of claim 1, wherein the mask further comprises a stereo speaker to emit audio pertaining to the certain information.

13. The system of claim 1, wherein the mask further comprises one or more sensors to provide information related to geographical position, pose of the user, rotational rate of pose of the user, or some combination thereof.

14. The system of claim 1, wherein the mask further comprises one or more sensors comprising vocation imaging band specific cameras, visual band cameras, stereo microphones, acoustic sensors, or some combination thereof.

15. The system of claim 1, wherein the mask further comprises an optical bench that aligns the virtual retinal display to one or more eyes of the user.

16. The system of claim 1, wherein the processing device executes the instructions to superposition the certain information on a display.

17. The system of claim 1, wherein the mask is configured to operate across both visible light and high intensity ultraviolet light conditions.

18. The system of claim 1, wherein the processing device is configured to record the certain information, communications with other devices, or both.

19. The system of claim 1, wherein the mask provides protection against welding flash.

20. The system of claim 1, wherein the processing device executes the instructions to map the mask in a physical space in which the mask is located.

21. The system of claim 1, wherein the mask comprises goggles.

22. A mask configured to be worn by a user, wherein the mask comprises:

a virtual retinal display;

a memory device storing instructions;

a processing device communicatively coupled to the memory device and the virtual retinal display, wherein the processing device executes the instructions to:

execute an artificial intelligence agent trained to perform at least one or more functions to determine certain information, wherein the one or more functions comprise:

identifying perception-based objects and features, determining cognition-based scenery to identify one or more material defects, one or more assembly defects, one or more acceptable features, or some combination thereof, and determining one or more recommendations, instructions, or both; and cause the certain information to be presented via the virtual retinal display on one or more retina of the user.

23. The mask of claim 22, wherein the virtual retinal display projects an image onto at least one iris of the user to display alphanumeric data, graphic instructions, animated instructions, video instructions, or some combination thereof.

24. The mask of claim 22, wherein the mask further comprises a network interface configured to enable bidirectional communication with a second network interface of a second mask, and the bidirectional communication enables transmission of real-time or near real-time audio and video data, recorded audio and video data, or some combination thereof.

25. The mask of claim 24, further comprising a peripheral haptic device, wherein:

the mask further comprises a haptic interface, and wherein the haptic interface is configured to perform bidirectional haptic sensing and stimulation using the peripheral haptic device and the bidirectional communication, and wherein the stimulation comprises performing mimicked gestures via the peripheral haptic device.

26. The mask of claim 24, wherein the bidirectional communication enables a master user of the second mask to view and/or listen to the real-time or near real-time audio and video data, recorded audio and video data, or some combination thereof, and to provide instructions to the user via the mask.

27. The mask of claim 22, wherein bidirectional communication enables the user of the mask to provide instructions to a plurality of students via a plurality of masks.

28. The mask of claim 22, wherein bidirectional communication enables the user of the mask to provide instructions to a plurality of students via a plurality of computing devices.

29. A computer-implemented method comprising:

executing, by one or more processing devices of a mask, an artificial intelligence agent trained to perform at least one or more functions to determine certain information, wherein the one or more functions comprise:

identifying perception-based objects and features, determining cognition-based scenery to identify one or more material defects, one or more assembly defects, one or more acceptable features, or some combination thereof, and determining one or more recommendations, instructions, or both; and causing, by the one or more processing devices, the certain information to be presented via a virtual retinal display of the mask on one or more retina of the user.

30. A tangible, non-transitory computer-readable medium storing instructions that, when executed, cause a processing device to:

execute, by one or more processing devices of a mask, an artificial intelligence agent trained to perform at least one or more functions to determine certain information, wherein the one or more functions comprise:

identifying perception-based objects and features, determining cognition-based scenery to identify one or more material defects, one or more assembly defects, one or more acceptable features, or some combination thereof, and determining one or more recommendations, instructions, or both; and cause, by the one or more processing devices, the certain information to be presented via a virtual retinal display of the mask.

* * * * *